US011478133B2

(12) United States Patent
Kasai et al.

(10) Patent No.: US 11,478,133 B2
(45) Date of Patent: Oct. 25, 2022

(54) MEDICAL OBSERVATION SYSTEM, APPARATUS FOR CONTROLLING THE SAME, AND METHOD FOR CONTROLLING THE SAME

(71) Applicant: Sony Corporation, Tokyo (JP)

(72) Inventors: Takara Kasai, Kanagawa (JP); Yohei Kuroda, Tokyo (JP); Takeshi Maeda, Tokyo (JP); Seiji Wada, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 526 days.

(21) Appl. No.: 16/486,503

(22) PCT Filed: Jan. 22, 2018

(86) PCT No.: PCT/JP2018/001842
§ 371 (c)(1),
(2) Date: Aug. 16, 2019

(87) PCT Pub. No.: WO2018/159155
PCT Pub. Date: Sep. 7, 2018

(65) Prior Publication Data
US 2020/0046208 A1    Feb. 13, 2020

(30) Foreign Application Priority Data

Feb. 28, 2017 (JP) .............................. JP2017-035964
Nov. 7, 2017 (JP) .............................. JP2017-215117

(51) Int. Cl.
*A61B 1/00* (2006.01)
*A61B 34/30* (2016.01)
(Continued)

(52) U.S. Cl.
CPC ...... *A61B 1/00149* (2013.01); *A61B 1/00006* (2013.01); *A61B 1/00039* (2013.01);
(Continued)

(58) Field of Classification Search
CPC ............ A61B 1/00149; A61B 1/00006; A61B 1/00039; A61B 1/00045; A61B 1/00154;
(Continued)

(56) References Cited

U.S. PATENT DOCUMENTS

2002/0156345 A1* 10/2002 Eppler ............... A61B 1/00147
600/102
2011/0028992 A1* 2/2011 Geiger ................... A61B 34/70
606/130

(Continued)

FOREIGN PATENT DOCUMENTS

JP      2002-123291 A    4/2002
JP      2009-524498 A    7/2009
(Continued)

OTHER PUBLICATIONS

International Search Report and Written Opinion dated Feb. 13, 2018 for PCT/JP2018/001842 filed on Jan. 22, 2018, 11 pages including English Translation of the International Search Report.

Primary Examiner — Timothy J Neal
Assistant Examiner — William B Chou
(74) Attorney, Agent, or Firm — Xsensus LLP

(57) ABSTRACT

A medical observation system includes a multi-link structure in which a plurality of links is mutually coupled by joint parts, a medical observation apparatus attached on the multi-link structure, a control part configured to control the multi-link structure or the medical observation apparatus, and a user interface part by which a user inputs an instruction to change a visual field of the medical observation apparatus. When a user instructs to move a visual field of the medical observation apparatus vertically or horizontally, to rotate an oblique-viewing endoscope, or to change a mag-
(Continued)

nification of the visual field via the user interface part, the control part controls the multi-link structure or the medical observation apparatus.

21 Claims, 29 Drawing Sheets

(51) Int. Cl.
*A61B 1/313* (2006.01)
*G06F 3/16* (2006.01)

(52) U.S. Cl.
CPC ...... *A61B 1/00045* (2013.01); *A61B 1/00154* (2013.01); *A61B 1/00179* (2013.01); *A61B 1/00188* (2013.01); *A61B 1/3132* (2013.01); *G06F 3/167* (2013.01); *A61B 2034/301* (2016.02)

(58) Field of Classification Search
CPC ............ A61B 1/00179; A61B 1/00188; A61B 1/3132; A61B 2034/301; G06F 3/167
See application file for complete search history.

(56) References Cited

U.S. PATENT DOCUMENTS

| | | | |
|---|---|---|---|
| 2014/0088361 | A1 | 3/2014 | Hrayr et al. |
| 2015/0332196 | A1* | 11/2015 | Stiller .................... G16H 70/20 705/2 |
| 2016/0007836 | A1* | 1/2016 | Kikuchi ............. A61B 1/00009 600/102 |
| 2016/0353969 | A1* | 12/2016 | Kikuchi ................. A61B 34/20 |
| 2017/0212723 | A1* | 7/2017 | Atarot .................... G06F 3/167 |

FOREIGN PATENT DOCUMENTS

| | | |
|---|---|---|
| JP | 2015-107249 A | 6/2015 |
| JP | 2016-87141 A | 5/2016 |
| WO | 2014/156218 A1 | 10/2014 |
| WO | 2017/010198 A1 | 1/2017 |
| WO | 2017/145475 A1 | 8/2017 |

\* cited by examiner

FIG. 3
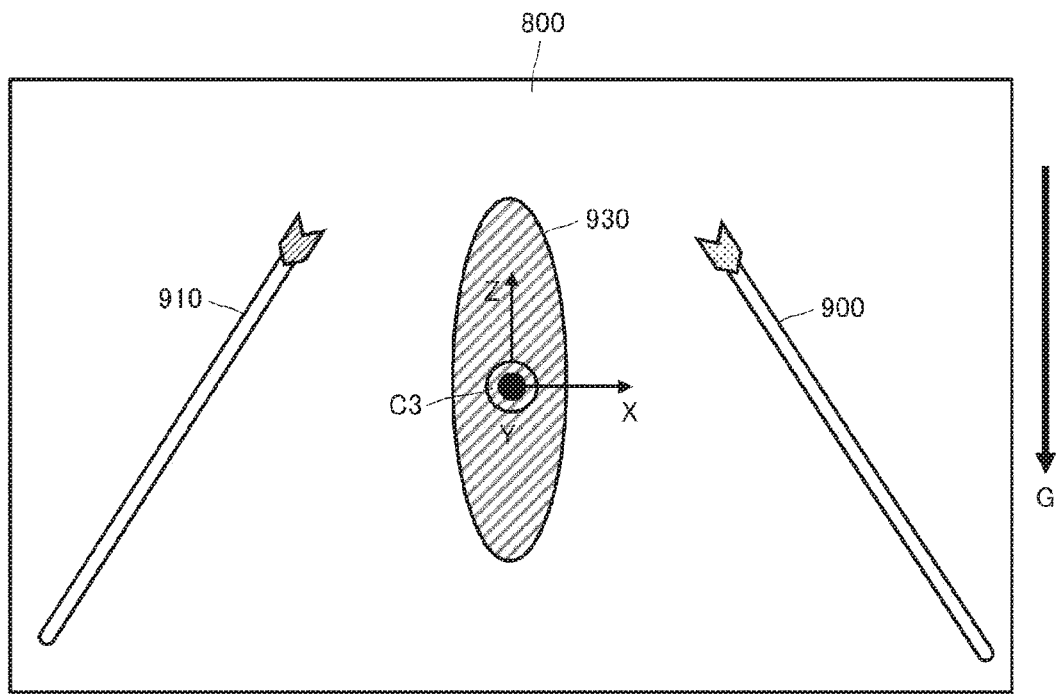
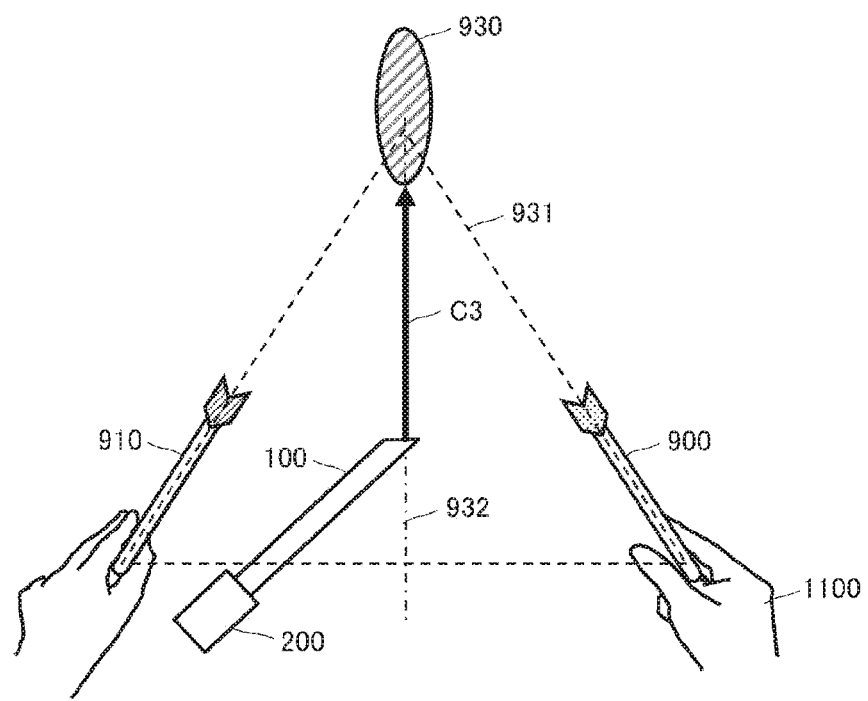

FIG. 7
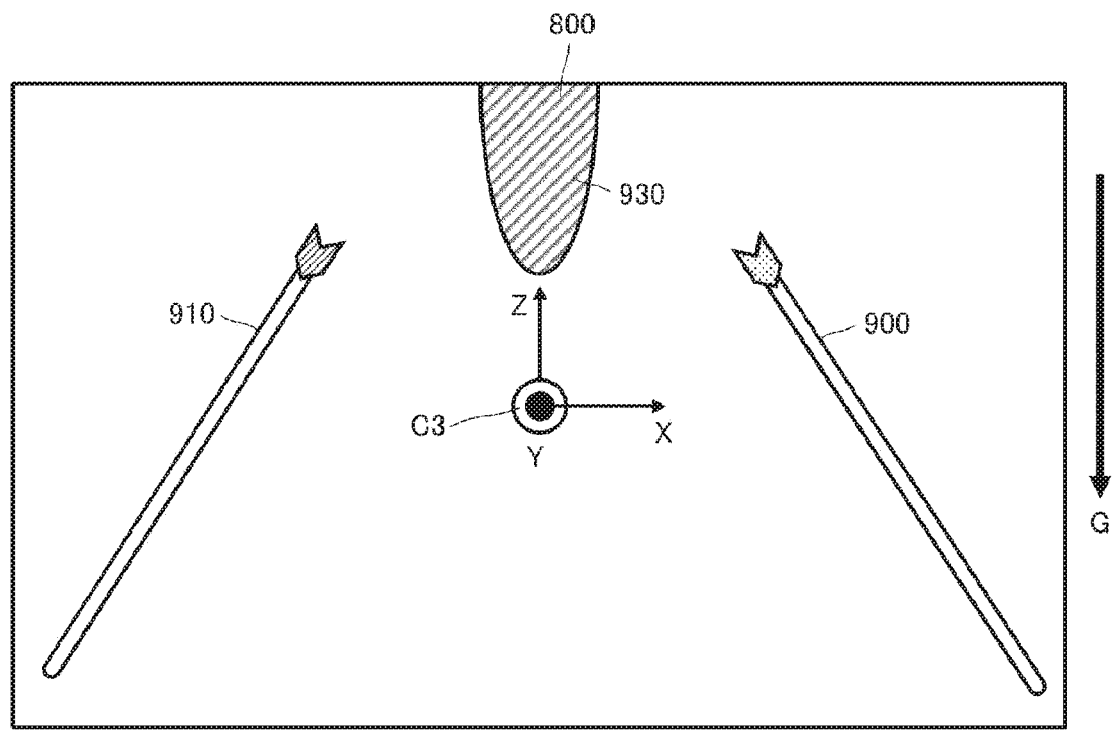
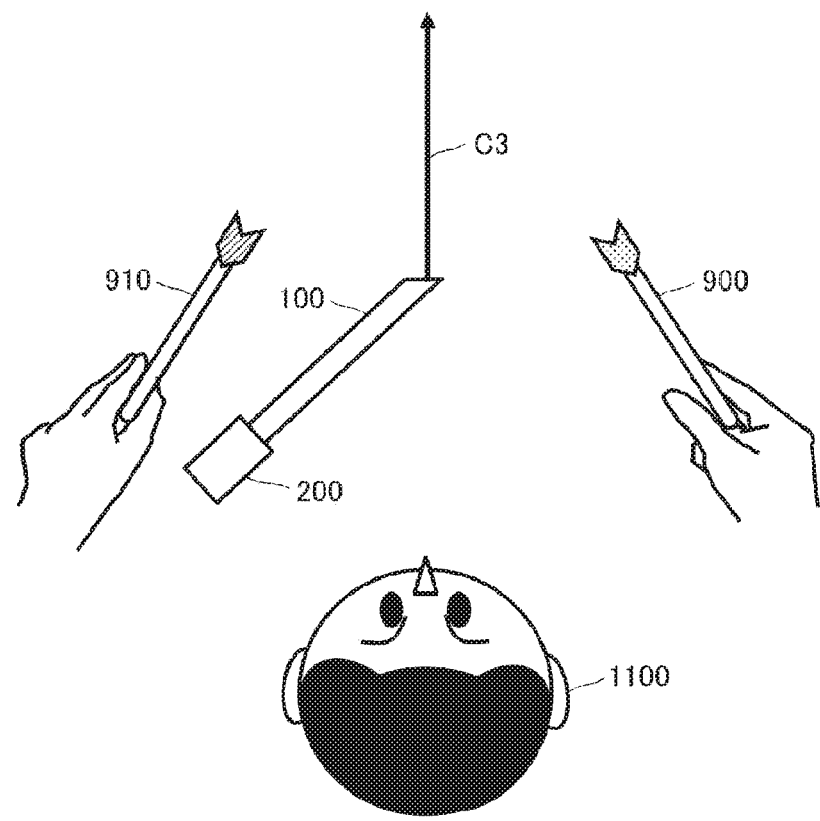

FIG. 8
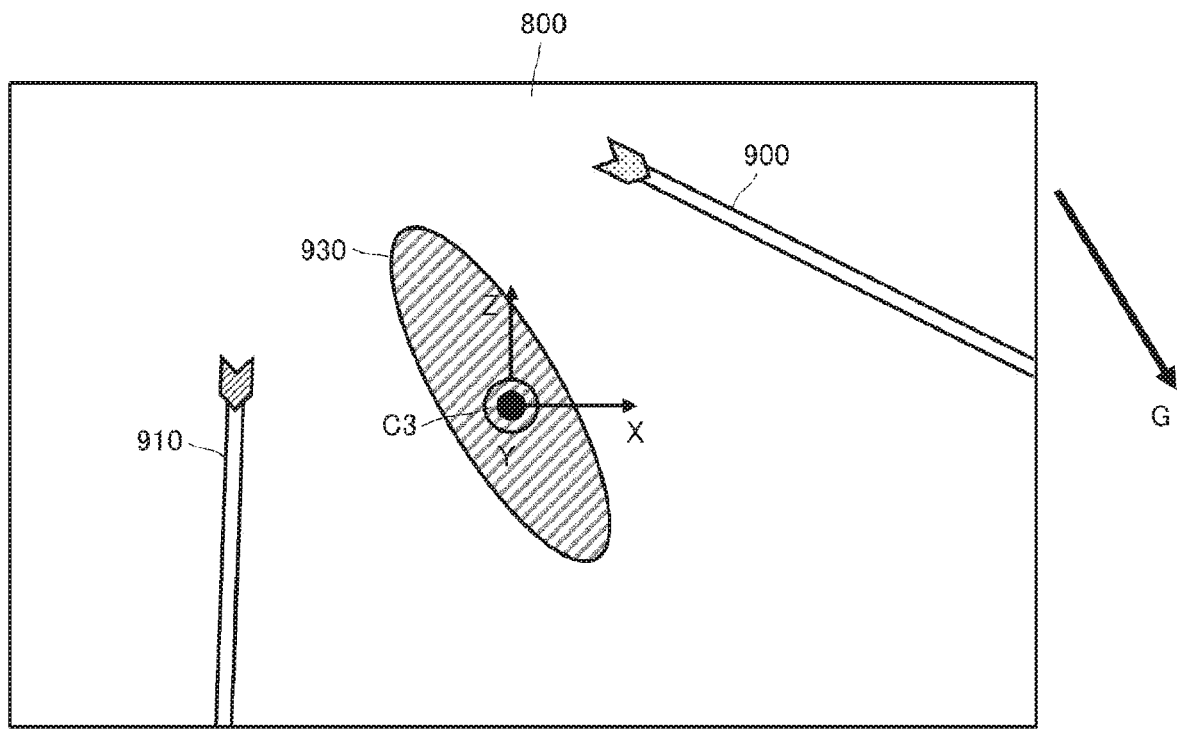
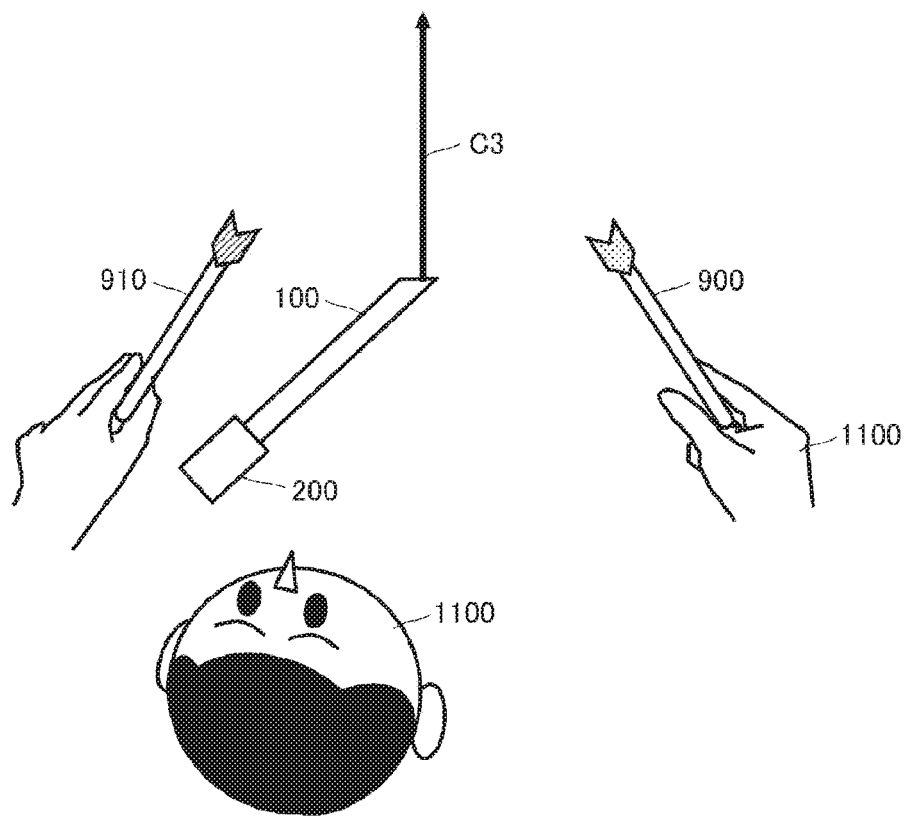

FIG. 9
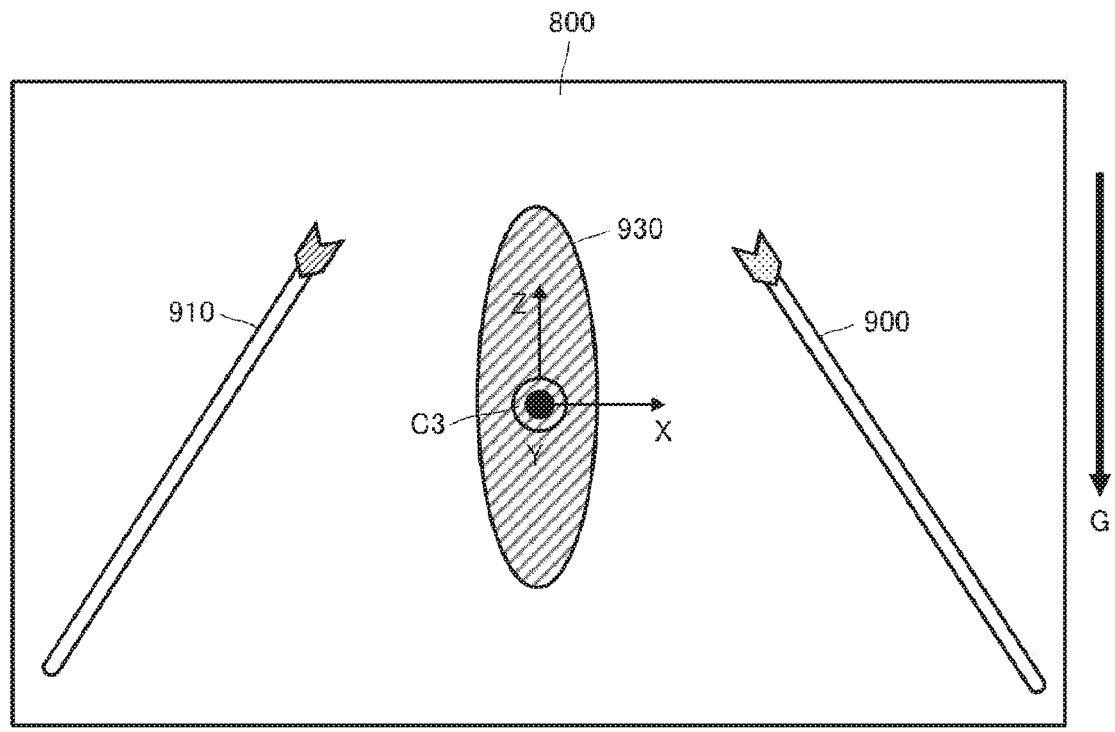
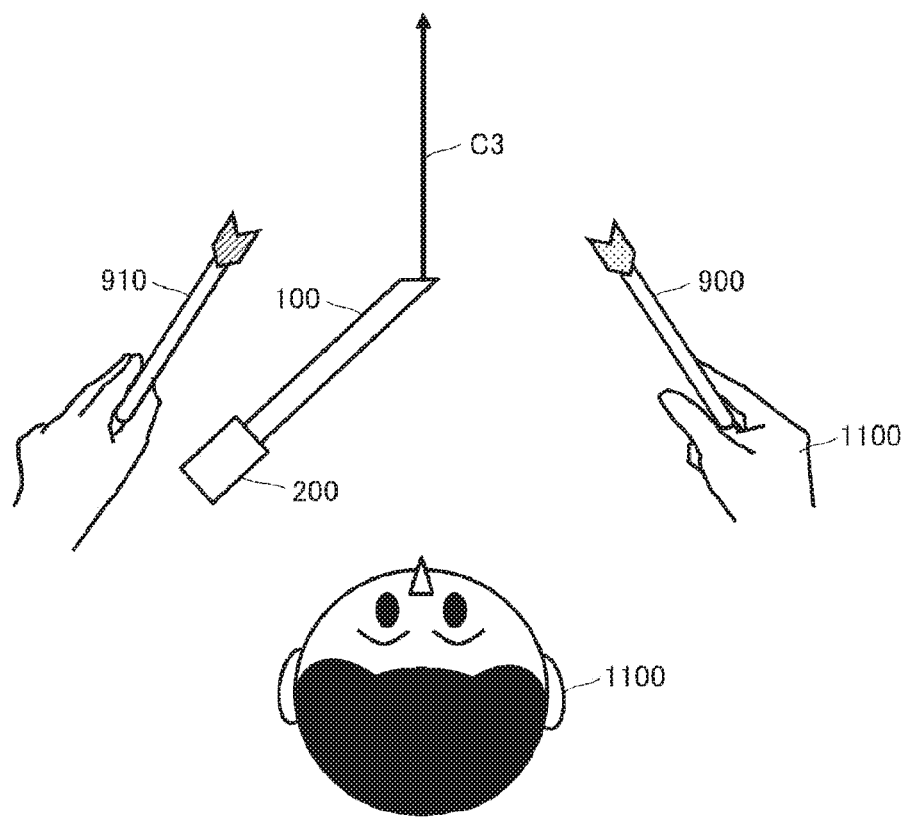

FIG. 11
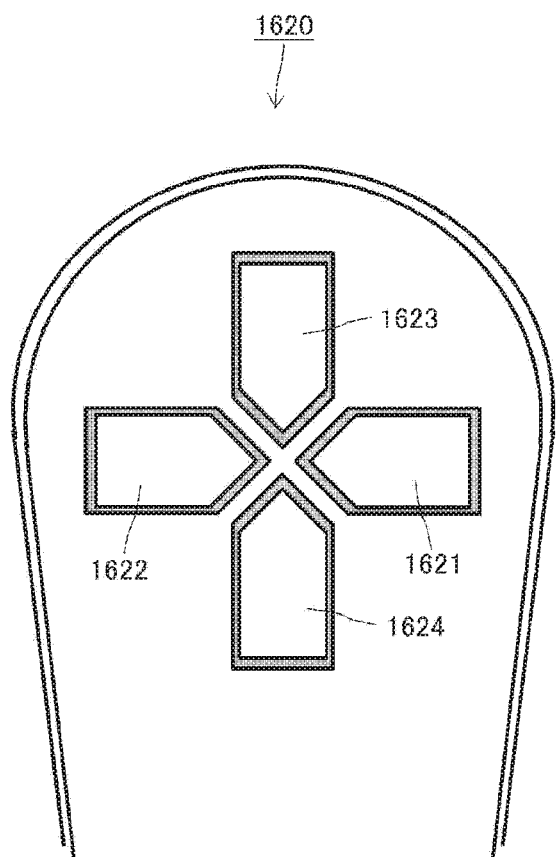
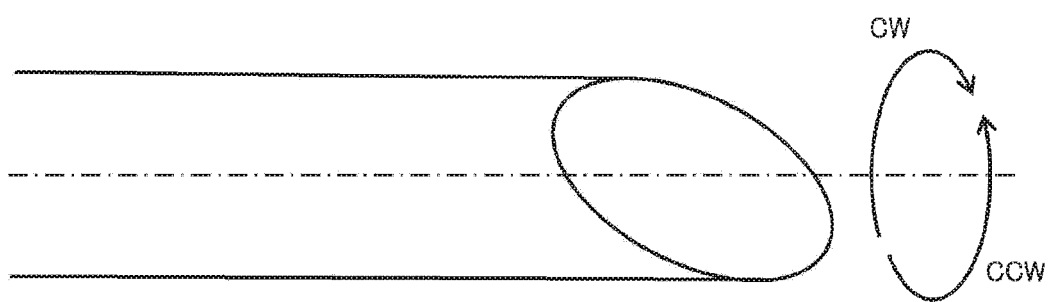

| Upper Right | Upper | Upper Left |
|---|---|---|
| Right |  | Left |
| Lower Right | Lower | Lower Left |

MEDICAL OBSERVATION SYSTEM, APPARATUS FOR CONTROLLING THE SAME, AND METHOD FOR CONTROLLING THE SAME

CROSS-REFERENCE TO RELATED APPLICATIONS

The present application is based on PCT filing PCT/JP2018/001842, filed Jan. 22, 2018, which claims priority to JP 2017-035964, filed Feb. 28, 2017, and JP 2017-215117, filed Nov. 7, 2017, the entire contents of each are incorporated herein by reference.

TECHNICAL FIELD

The technology disclosed in the present specification relates to a medical observation system, an apparatus for controlling the medical observation system, and a method for controlling the same.

BACKGROUND ART

An endoscope as an exemplary observation apparatus is configured of a shooting part which is inserted into an object to be observed thereby to acquire an observation image, and a display apparatus for displaying the acquired observation image, and is widely used in various industrial fields including medical field. A medical system in which an endoscope is attached on the tip of an arm has been developed in recent years. The medical system has the advantage, for example, that the robotics technology is introduced into at least some human works thereby to realize higher working accuracy and higher efficiency.

Endoscopes include a flexible scope using a flexible material, and a rigid scope configured of a rigid lens tube including a metal or the like. The rigid scope displays an object to be observed several millimeters to several centimeters away. Typically, a rigid scope is used for intra-abdominal surgery and the like. Specifically, a rigid scope is inserted into the abdominal cavity via a tube called trocar. At this time, the rigid scope pivots on the trocar.

Further, the kinds of rigid scopes may include a forward-viewing endoscope in which an optical axis of the rigid scope matches with an axial direction of the lens tube (the lens faces in the front direction), and an oblique-viewing endoscope in which an optical axis of the rigid scope is tilted relative to an axis of the lens tube (see Patent Document 1, for example).

CITATION LIST

Patent Document

Patent Document 1: Japanese Patent Application Laid-Open No. 2016-87141

SUMMARY OF THE INVENTION

Problems to be Solved by the Invention

It is an object of the technology disclosed in the present specification to provide a medical observation system with improved operability, an apparatus for controlling an endoscope system, and a method for controlling the same.

Solutions to Problems

The technology disclosed in the present specification has been made in consideration of the above problem, and a first aspect thereof is a medical observation system including:
- an arm capable of holding a medical observation apparatus used for observing a diseased site;
- a control part configured to control the arm or the medical observation apparatus; and
- a user interface part by which a user inputs an instruction to change a visual field of the medical observation apparatus,
- in which the control part controls the arm or the medical observation apparatus in response to the instruction to change the visual field of the medical observation apparatus via the user interface part.

The user interface part includes a first operator by which a user inputs an instruction to move the visual field of the medical observation apparatus in any direction. Then, the control part controls a motion of the arm to move the visual field of the medical observation apparatus in a direction corresponding to an instructed moving direction according to an operation of the first operator.

Further, the medical observation apparatus can be an oblique-viewing endoscope in which an optical axis of an objective optical system is tilted relative to an optical axis of an eyepiece optical system (a lens tube axis of a scope) at a predetermined angle and which is rotatable around the lens tube axis. In such a case, the user interface part further includes a second operator by which the user instructs the visual field direction of the oblique-viewing endoscope, and the control part may control a rotation angle around a lens barrel axis of the oblique-viewing endoscope according to an operation of the second operator.

Moreover, the user interface part further includes a third operator configured to input an instruction to zoom in or out the endoscope, and the control part may control a motion of the multi-link structure to zoom in or out a visual field of the endoscope according to an operation of the third operator. In a case where the endoscope is an oblique-viewing endoscope in which an optical axis of an objective optical system is tilted relative to a lens tube axis at a predetermined angle, the control part may control a motion of the arm such that a distance between the oblique-viewing endoscope and an object to be observed accords a magnification instructed via the user inter face part under a constraint condition that the oblique-viewing endoscope is inserted into the abdominal cavity via a trocar and pivots on the trocar.

Further, a second aspect of the technology disclosed in the present specification is a control apparatus including:
- a user interface part configured to input an instruction to change a visual field of a medical observation apparatus held by an arm; and
- a control part configured to control the arm or the medical observation apparatus,
- in which the control part controls the arm or the medical observation apparatus when instructed to change the visual field of the medical observation apparatus via the user interface part.

Further, a third aspect of the technology disclosed in the present specification is a control method including:
- a user input step of inputting an instruction to change a visual field of a medical observation apparatus held by an arm; and
- a control step of controlling the arm or the medical observation apparatus, in which the arm or the medical observation apparatus is controlled in the control step when an instruction to change the visual field of the medical observation apparatus is made in the user input step.

Effects of the Invention

According to the technology disclosed in the present specification, it is possible to provide a medical observation system with improved operability, an apparatus for controlling an endoscope system, and a method for controlling the same.

Additionally, the effects described in the present specification are merely exemplary and the effects of the present invention are not limited thereto. Further, the prevent invention may obtain additional effects other than the above effect.

The other objects, characteristics, and advantages of the technology disclosed in the present specification will be apparent from the more detailed description based on the embodiments described below or the accompanying drawings.

BRIEF DESCRIPTION OF DRAWINGS

FIG. 3 is a diagram schematically illustrating an exemplary method for using the medical observation system 1000.

FIG. 7 is a diagram illustrating an image of the oblique-viewing endoscope displayed on a monitor screen 800, and an operator 1100 observing the monitor screen 800.

FIG. 8 is a diagram illustrating an image of the oblique-viewing endoscope displayed on the monitor screen 800, and the operator 1100 observing the monitor screen 800.

FIG. 9 is a diagram illustrating an image of the oblique-viewing endoscope displayed on the monitor screen 800, and the operator 1100 observing the monitor screen 800.

FIG. 11 is a diagram illustrating other exemplar)/configuration of an input apparatus 1620 applied to the user interface part 160.

MODE FOR CARRYING OUT THE INVENTION

Embodiments of the technology disclosed in the present specification will be described below in detail with reference to the accompanying drawings.

Figure 1:
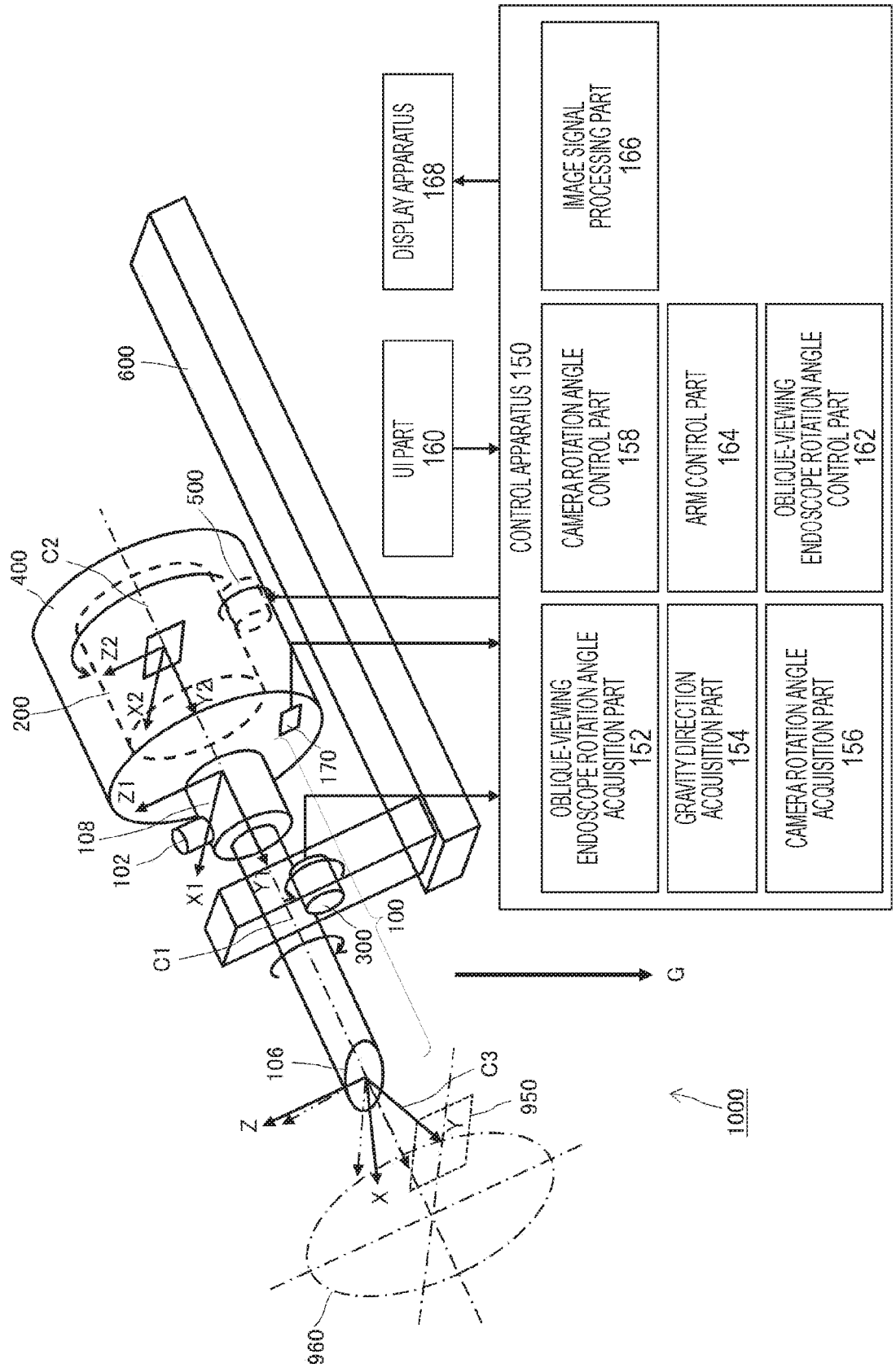
FIG. 1 is a perspective view illustrating an exemplary configuration of a medical observation system 1000.

FIG. 1 illustrates an exemplary configuration of a medical observation system 1000 to which the technology disclosed in the present specification is applicable.

The illustrated medical observation system 1000 is assumed to be used for a medical system for performing intra-abdominal surgery and the like, for example, and a so-called rigid scope is applied therefor. The medical observation system 1000 includes a lens tube 100 and a camera 200. The oblique-viewing endoscope 100 and the camera 200 are connected such that an optical axis C1 of an eyepiece optical system of the lens tube 100 matches with an optical axis C2 of a shooting optical system of the camera 200. The lens tube of an endoscope includes a forward-viewing endoscope and an oblique-viewing endoscope, and an oblique-viewing endoscope is used for the lens tube 100 in the medical observation system 1000 according to the present embodiment (the lens tube 100 will be also called oblique-viewing endoscope 100 below).

The oblique-viewing endoscope 100 includes a light guide connector 102 for attaching a light guide (not illustrated), and an eyepiece part 108 connected to the camera 200. Further, an objective lens part 106 is arranged at the distal end of the oblique-viewing endoscope 100. An optical axis C3 of an objective optical system of the objective lens part 106 is tilted at a predetermined, angle relative to the optical axis C1 of the eyepiece optical system.

The tip of the oblique-viewing endoscope 100 is inserted into the abdominal cavity via a trocar (not illustrated) punctured into the abdominal wall of a patient, for example, for use. The light guide attached on the light guide connector 102 is extended inside the oblique-viewing endoscope 100. Light generated by a light source (not illustrated) such as light emitting diode (ED) or laser is guided to the tip of the oblique-viewing endoscope 100 by the light guide to be irradiated toward an object to be observed in the abdominal cavity of the patient via the objective lens part 106.

Further, the oblique-viewing endoscope 100 is rotatably supported around the optical axis C1 of the eyepiece optical system by a holding part 600, and rotates around the optical axis C1 of the eyepiece optical system relative to the holding part 600 by a driving force of an oblique-viewing endoscope rotation apparatus 300. The oblique-viewing endoscope rotation apparatus 300 includes a motor for generating a driving force, an encoder for detecting a rotation angle of an output shaft of the motor, and the like. However, the oblique-viewing endoscope rotation apparatus 300 may be configured to rotate the oblique-viewing endoscope 100 not electrically by use of the motor but manually.

When the holding part 600 is driven, the oblique-viewing endoscope 100 moves forward or backward in the abdominal cavity via a tubular opening instrument punctured into the abdominal wall, called trocar (not illustrated), and pivots on the trocar (or such that a position where the oblique-viewing endoscope 100 passes through the trocar does not move) so that the objective lens part 106 at the tip thereof moves inside the abdominal cavity. For example, in a case where the holding part 600 drives and moves the oblique-viewing endoscope 100 in parallel with the optical axis C1 of the eyepiece optical system, a direction in which the oblique-viewing endoscope 100 is inserted matches with the optical axis C1 direction of the eyepiece optical system.

Further, the oblique-viewing endoscope 100 rotates around the optical axis C1 of the eyepiece optical system relative to the holding part 600 and the optical axis C3 of the objective optical system of the objective lens part 106 also rotates around the optical axis C1 of the eyepiece optical system by a driving force of the oblique-viewing endoscope rotation apparatus 300. For example, in a case where a camera visual field 950 corresponding to a shooting amount region of the camera 200 described below is present ahead by a predetermined distance in the optical axis C3 direction from the objective lens part 106, the center of the camera visual field 950 moves along with the rotation around the optical axis C1 of the eyepiece optical system while drawing a rotation movement trajectory indicated by a reference numeral 960.

The camera 200 includes a shooting device 204 stored in a casing (camera head) 400 and directed for shooting an image of the oblique-viewing endoscope 100, and a shooting optical system (not illustrated) arranged in front of the shooting device 204. The shooting device 204 may be a complementary metal oxide semiconductor (CMOS) type image sensor, for example, and employs a device capable of color photography in the Bayer layout. For example, a shooting device for shooting an image with a high resolution of 4K or higher may be used for the camera 200. Further, the camera 200 may be provided with a plurality of shooting devices for stereoscopic viewing (3D display). Additionally, the camera 200 mounts thereon a mechanism for driving the shooting optical system as needed and adjusting a magnification and a focal length.

Reflected light (observation light) from an object to be observed irradiated with light via the light guide is condensed into the shooting device 204 closer to the shooting optical system. The shooting device 204 then photoelectrically converts the received observation light and generates an electric signal or an image signal corresponding to the observation image. The camera 200 outputs the image signal as RAW data.

The camera 200 is supported in the casing 400 to be rotatable around the optical axis C2 of the shooting optical system. The camera 200 rotates around the optical axis C2 of the shooting optical system relative to the casing 400 by a driving force of a camera rotation apparatus 500. The camera rotation apparatus 500 includes a motor for generating a driving force, an encoder for detecting a rotation angle of an output shaft of the motor, and the like.

A gravity sensor 170 is arranged on an end face of the casing 400 on the eyepiece part 108 side, and can sense the direction of gravity G In a case where the medical observation system 1000 is attached on a support arm apparatus (as described below) for use, for example, a posture of the medical observation system 1000 changes in use, but the gravity sensor 170 can always sense the direction of gravity G. Additionally, a place where the gravity sensor 170 is arranged is not limited to the illustrated example.

The medical observation system 1000 further includes a control apparatus 150. A detailed configuration of the control apparatus 150 will be described below. Further, the medical observation system 1000 is connected with a display apparatus 168 for displaying an image (or image shot by the shooting device 204) acquired by the oblique-viewing endoscope 100 and the camera 200. An operator as a user of the medical observation system 1000 can operate medical instruments such as forceps, tweezers, and cutting instrument thereby to treat a diseased site while observing an image of the diseased site in the abdominal cavity displayed on the monitor screen of the display apparatus 168.

In FIG. 1, a distal direction of the optical axis C3 of the objective optical system is defined as a positive Y-axis direction, a vertically-upward direction orthogonal to the Y-axis on the plane of the objective lens part 106 orthogonal to the Y-axis substantially-relative direction to the gravity G) is defined as a positive Z-axis direction, and a horizontally-rightward direction orthogonal to the Z-axis on the same plane (the right side to the positive Y-axis direction) is defined as a positive X-axis direction.

Further, a distal direction of the optical axis C1 of the eyepiece optical system is defined as a positive Y1-axis direction, a vertically-upward direction orthogonal to the Y1-axis on the plane of the eyepiece part 108 orthogonal to the Y1-axis (a substantially-relative direction to the gravity G) is defined as a positive Z1-axis direction, and a horizontally-rightward direction orthogonal to the Z1-axis on the same plane (the right side to the positive Y1-axis direction) is defined as a positive X1-axis direction.

Further, a distal direction of the shooting optical system arranged in front of the shooting device 204 is defined as a positive Y2-axis direction, a vertically-upward direction orthogonal to the Y2-axis on the plane (shooting plane) of the shooting device 204 orthogonal to the Y2-axis (a substantially-relative direction to the gravity G) is defined as a positive Z2-axis direction, and a horizontally-rightward direction orthogonal to the Z1-axis on the same plane (the right side to the positive Y2-axis direction) is defined as a positive X2-axis direction.

Figure 2:
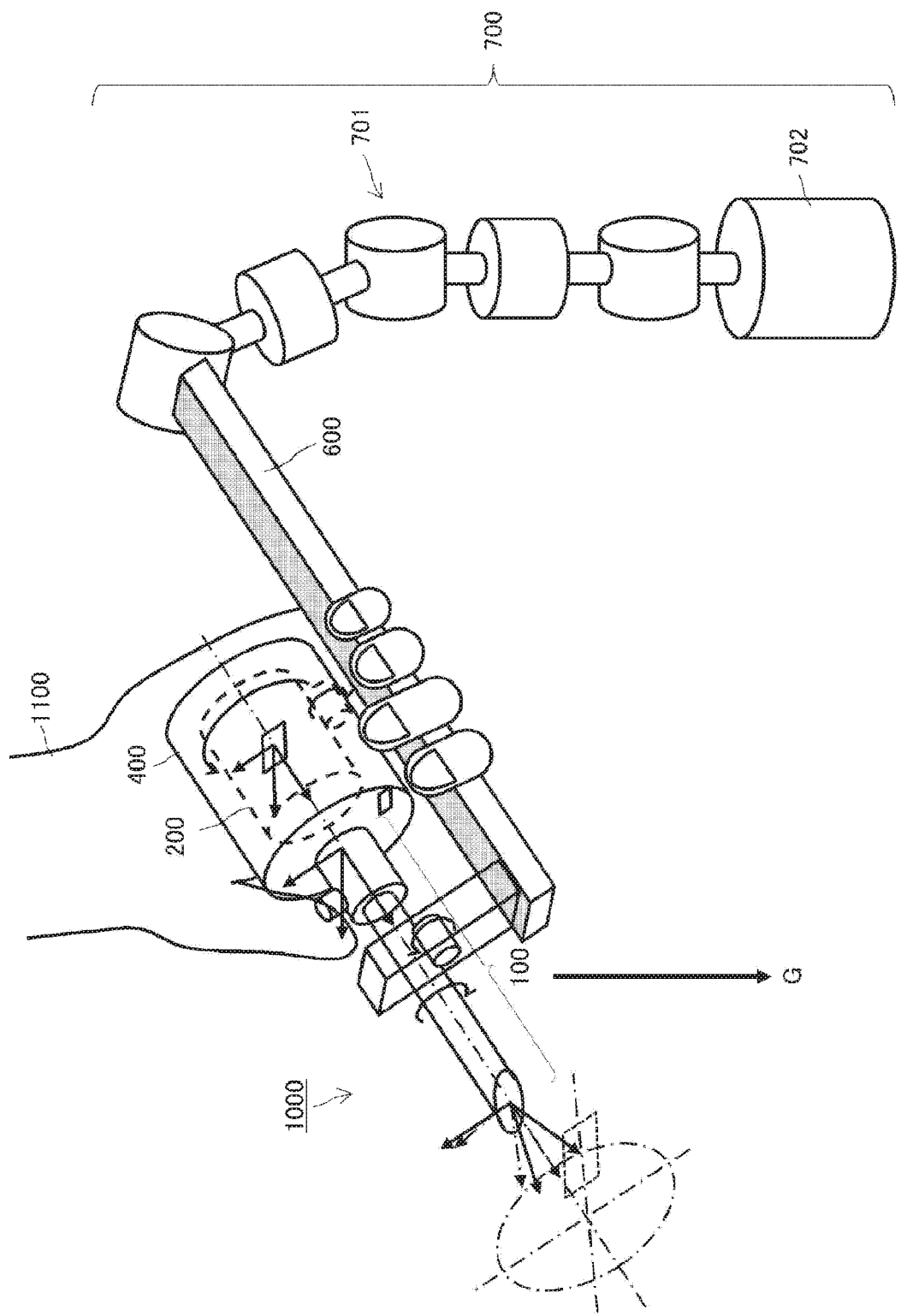
FIG. 2 is a diagram schematically illustrating an exemplary configuration of a support arm apparatus 700 attached with the medical observation system 1000.

FIG. 2 illustrates how the medical observation system 1000 is attached at the distal end of the support arm apparatus 700 as a form of using the medical observation system 1000 illustrated in FIG. 1. The support arm apparatus 700 is also called scope holder, endoscope holder, or holder arm.

As illustrated in FIG. 2, the holding part 600 supports the medical observation system 1000 at the distal end of the support arm apparatus 700. The support arm apparatus 700 drives either electrically or manually. Further, as illustrated in FIG. 2, a user 1100 such as an operator can directly grip the holding part 600 for operation. For example, in a manual operation mode (as described below), the support arm apparatus 700 is bent in accordance with an operation of the operator 1100, and is kept in the finally-bent state when the operator 1100 releases the holding part 600.

The support arm apparatus 700 is configured of a base part 702 as a base table, and an arm part 701 extending from the base part 702. FIG. 2 illustrates a simplified configuration of the arm part 701 for simplified drawing. Actually, the shapes, number, arrangements of links and joint parts, directions of the rotation shafts of the joint parts, and the like are set as needed such that the arm part 701 has a desired degree of freedom.

The arm part 701 illustrated in FIG. 2 is a u ink structure in which a plurality of links is mutually coupled by joint parts, and has six or more degrees of freedom, for example. Thereby, the medial observation system 1000 at the distal end can be freely moved within the movable range of the arm part 701, and the oblique-viewing endoscope 100 can be inserted into the abdominal cavity of a patient from a desired direction via a trocar (not illustrated).

Each joint part s provided with an actuator, and the joint part is rotatable around a predetermined rotation shaft when the actuator is driven. An arm control part 164 in the control apparatus 150 controls driving the actuator thereby to control the rotation angle of each joint part, to accordingly control driving the arm part 701, and to consequently realize controlling a position and a posture of the medical observation system 1000 (or the oblique-viewing endoscope 100).

For example, the arm control part 164 controls driving the arm part 701 in response to an input operation via a user interface (UI) 160 described below as needed, thereby controlling a position and a posture of the medical observation system 1000. By the controlling, the medical observation system 1000 at the distal end of the arm part 701 is moved to any position, and then can be fixedly supported at the position.

The support arm apparatus 700 is a medical system using the robotics technology, for example, in which the plurality of joint parts are controlled to rotate and to drive so that desired operations for surgeries such as intra-abdominal surgery are realized. The medical observation system 1000 and the support arm apparatus 700 may be handled as individual apparatuses, respectively, or the medical observation system 1000 may include the support arm apparatus 700 to be handled as one apparatus.

For example, a torque instruction value of each joint part for whole body cooperative control can be calculated and controlled in consideration of exercise purposes and constraint conditions for surgery by computations using generalized inverse kinematics. Further, disturbance torque due to a modelling error such as friction or inertia is estimated in torque-controlling each joint part, and a torque instruction value is corrected, thereby realizing ideal joint control of the joint part driving actuators. However, the whole body cooperative control of the support arm apparatus 700 or the ideal joint control of the joint parts is not directly associated with the technology disclosed in the present specification, and a detailed description thereof will be omitted.

FIG. 3 schematically illustrates an exemplary method for using the medical observation system 1000 according to the present embodiment. However, in the figure, it is assumed that right-hand forceps 900 and left-hand forceps 910, and additionally the oblique-viewing endoscope 100 of the medical observation system 1000 are inserted into the abdominal cavity via the trocars (not illustrated), respectively.

The medical observation system 1000 is connected with the display apparatus 168, and an image acquired by the oblique-viewing endoscope 100 and the camera 200 (or an image shot by the shooting device 204) is displayed on a monitor screen 800 of the display apparatus 168. The direction of gravity G of an object is displayed on the monitor screen 800 to match with the vertical direction of the screen. The operator 1100 can perform a surgery while observing an image of a diseased site in the abdominal cavity displayed on the monitor screen 800. Additionally, the optical axis C3 of the objective optical system of the objective lens part 106 rotates around the optical axis C1 of the eyepiece optical system (as described above), and a shot image is displayed on the monitor screen 800 such that the direction of gravity G of the object always matches with the vertical direction of the screen also while the optical axis C3 of the objective optical system is rotating.

Figure 4:
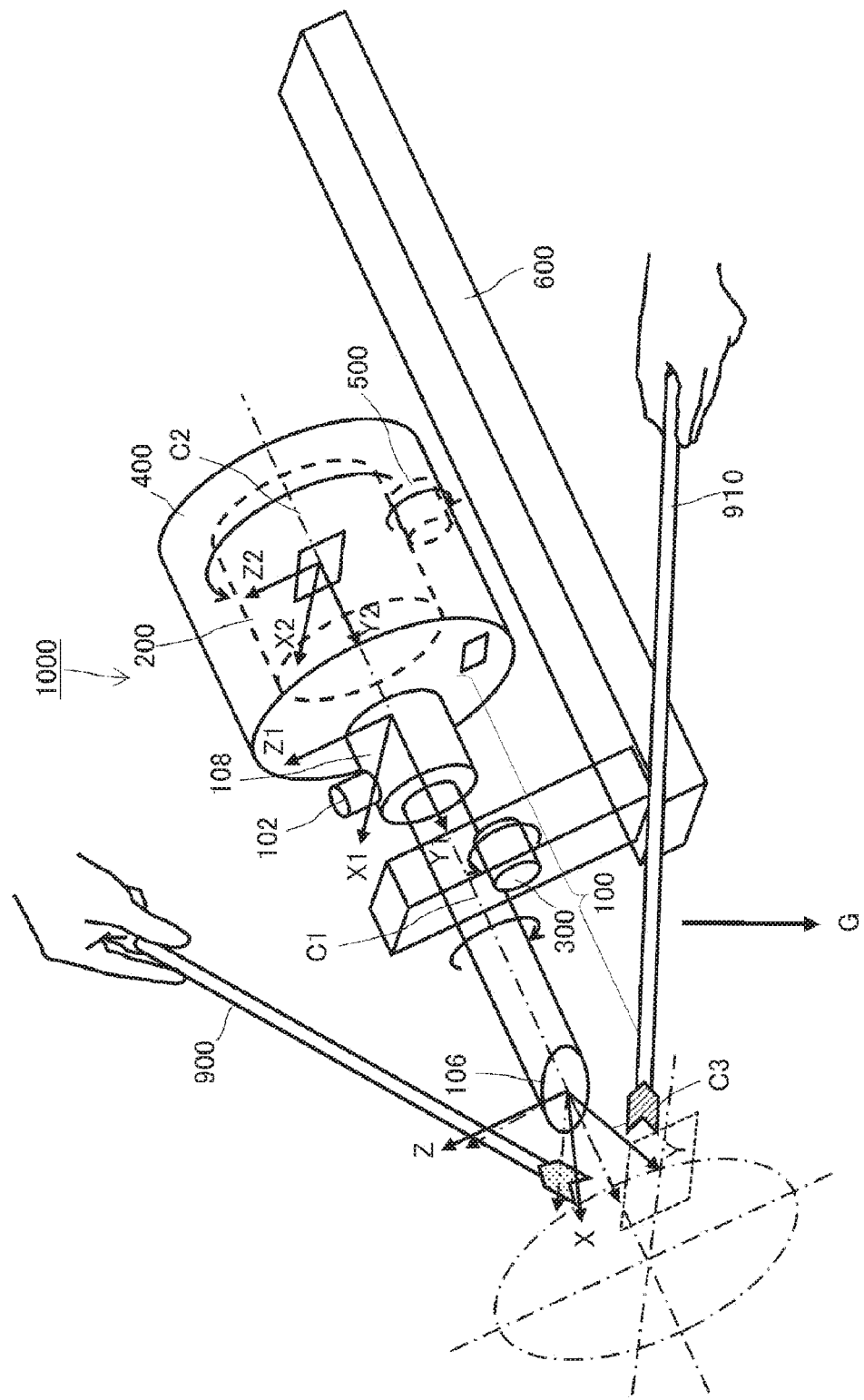
FIG. 4 is a diagram illustrating right-hand forceps 900 held by the right hand and left-hand forceps 910 held by the left hand overlapped on a perspective view of the medical observation system 1000, respectively.

The operator 1100 holds the right-hand forceps 900 with the right hand, and holds the left-hand forceps 910 with the left hand. As a reference, FIG. 4 illustrates the right-hand forceps 900 held with the right hand and the left-hand forceps 910 held with the left hand overlapped on a perspective view of the medical observation system 1000. A tissue to be treated 930 as a vertex, an operator as the base, and the right-hand forceps 900 and the left-hand forceps 910 as sides are arranged to configure an isosceles triangle 931, Then, the optical axis C3 of the objective optical system of the objective lens part 106 basically takes a visual field direction on the perpendicular bisector 932 of the isosceles triangle 931. Hand-eye coordination can be taken (an operation can be performed according to what a person see with his/her eyes) similarly to a surgery using forward-viewing endoscope in the basic positional relationship.

Figure 16:
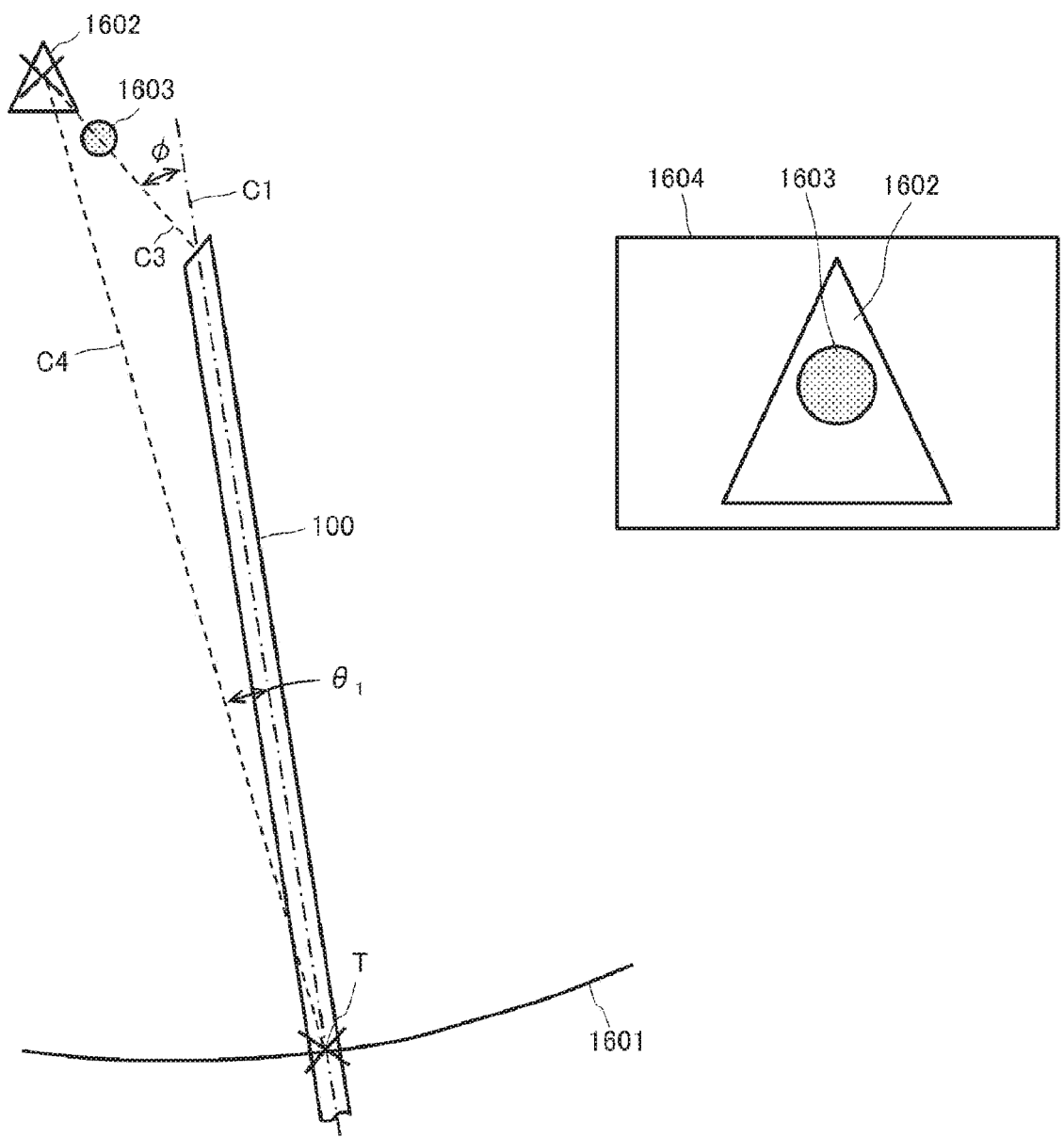
FIG. 16 is a diagram illustrating how the oblique-viewing endoscope 100 is inserted into the abdominal cavity from the abdominal wall 1601 to observe an object to be observed 1602.

Additionally, FIG. 3 and FIG. 4 illustrate that the operator 1100 grips the roots of the right-hand forceps 900 and the left-hand forceps 910 with the right hand and the left hand, respectively, for simplified drawing, but actually an operation for gripping the forceps may be performed by the handles at the roots of the right-hand forceps 900 and the left-hand forceps 910, FIG. 16 illustrates how the oblique-viewing endoscope 100 is inserted into the abdominal cavity from the abdominal wall 1601 to observe an object to be observed 1602. A trocar point T is a place where a trocar (not illustrated) is punctured into the abdominal wall 1601, and corresponds to a position where the oblique-viewing endoscope 100 is inserted into a human body. The reference numeral 1602 indicates an object to be observed by the oblique-viewing endoscope 100 (the medical observation system 1000), and a reference numeral 1603 indicates an obstacle such as organ. Further, C4 indicates a direction in which the trocar point T and the object to be observed 1602 are connected. In the example illustrated in FIG. 16, the oblique-viewing endoscope 100 is inserted into the abdominal cavity in a direction tilted at an angle $\theta_1$ clockwise from C4 on the Figure.

The optical axis C1 of the eyepiece optical system of the oblique-viewing endoscope 100 can be rotated with the trocar point 'T' as a fulcrum. Further, the oblique-viewing endoscope 100 can be moved forward or backward in the abdominal cavity from the trocar point T. Thus, a position and a posture of the oblique-viewing endoscope 100 can be changed in a combination of pivot of the oblique-viewing endoscope 100 on the trocar point T, and forward/backward movement. Further, as described above, the optical axis C3 of the objective optical system at the tip of the oblique-viewing endoscope 100 is tilted at a predetermined angle $\varphi$ relative to the optical axis C1 of the eyepiece optical system (the longitudinal direction of the oblique-viewing endoscope 100). Therefore, the oblique-viewing endoscope 100 is rotated around the optical axis C1 of the eyepiece optical system thereby to change the optical axis C3 direction of the objective optical system (or the line of sight direction of the camera 200). In short, the visual field of the camera 200 can be changed in a combination of pivot of the oblique-viewing endoscope 100 on the trocar point T, forward/backward movement thereof, and rotation of the oblique-viewing endoscope 100 around the optical axis C1 of the eyepiece optical system.

The obstacle 1603 is present between the objective lens 106 at the tip of the oblique-viewing endoscope 100 and the object to be observed 1602 at the position and the posture of the oblique-viewing endoscope 100 illustrated in FIG. 16. The object to be observed 1602 is hidden behind the obstacle 1603, and thus the entire region of the object to be observed 1602 cannot be observed in an image shot by the camera 200. A reference numeral 1604 indicates an image shot by the camera 200 in this state.

Figure 17:
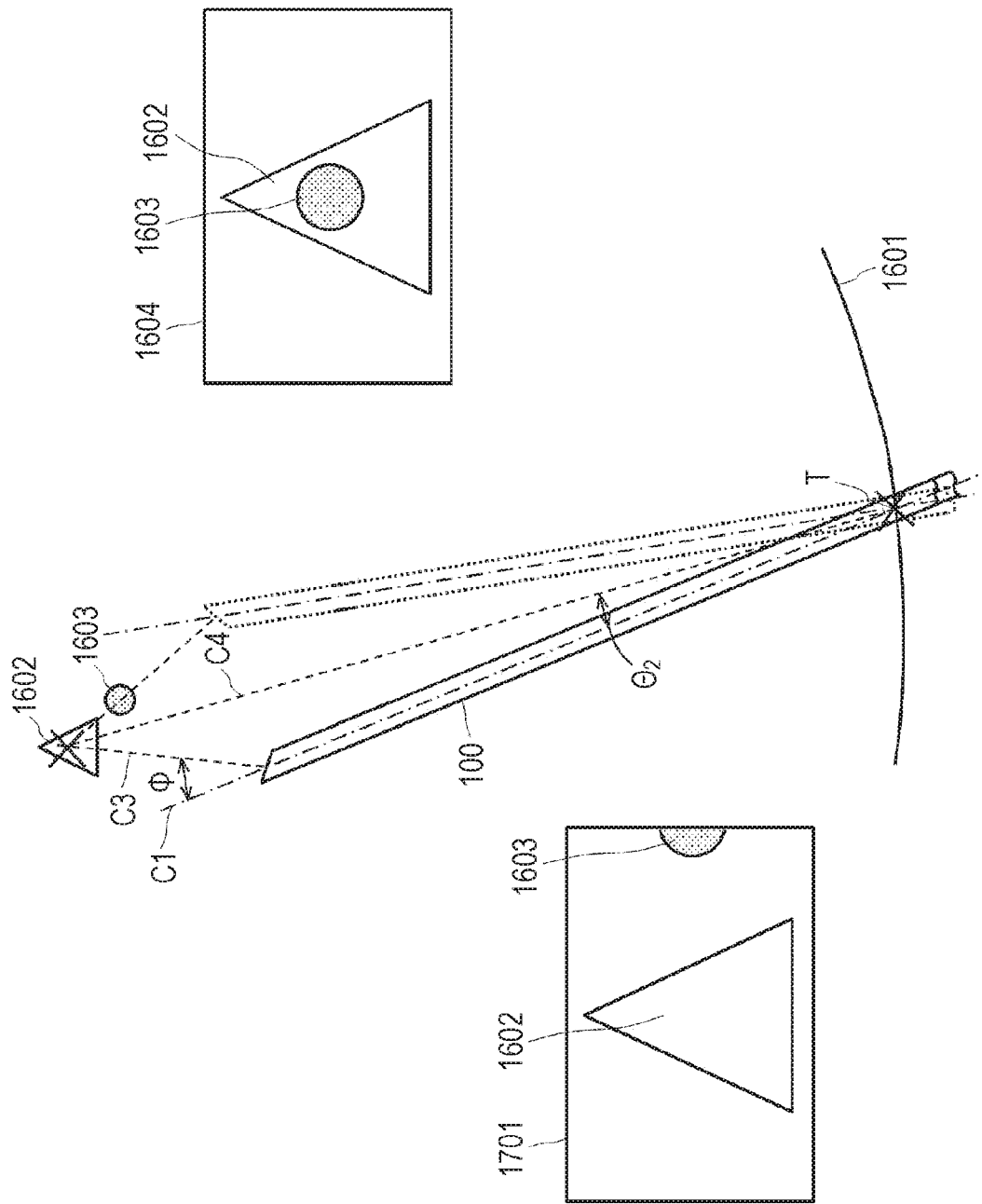
FIG. 17 is a diagram illustrating how the oblique-viewing endoscope 100 is inserted into the abdominal cavity from the abdominal wall 1601 to observe the object to be observed 1602.

FIG. 17 illustrates how the oblique-viewing endoscope 100 is changed in its position and posture and observes the object to be observed 1602 while being inserted into the abdominal cavity. The oblique-viewing endoscope 100 pivots on the trocar point T, and is tilted at an angle $\theta_2$ counterclockwise on the Figure from the C4 direction in which the trocar point T and the object to be observed 1602 are connected. Further, the oblique-viewing endoscope 100 is rotated around the optical axis of the eyepiece optical system thereby to adjust also the optical axis direction of the objective optical system as needed. The obstacle 1603 is deviated from an area between the objective lens 106 at the tip of the oblique-viewing endoscope 100 and the object to be observed 1602 in a state where the position, the posture, and the line of sight direction of the oblique-viewing endoscope 100 are changed as illustrated in FIG. 17. Thus, in an image shot by the camera 200, the entire region of the object to be observed 1602 cannot be observed without blockage of the obstacle 1603. A reference numeral 1701 indicates an image shot by the camera 200 in this state.

Additionally, the arm control part 164 drives and controls the actuator of each joint part of the support arm apparatus 700 in order to change the oblique-viewing endoscope 100 held by the holding part 600 at a desired position and posture. When the position and the posture illustrated in FIG. 16 are changed to the position and the posture illustrated in FIG. 17, the arm control part 164 drives and controls the actuator of each joint part of the support arm apparatus 700 such that the object to be observed 1602 is kept positioned at the center of an image shot by the camera 200 (or the optical axis of the objective optical system is kept facing the object to be observed 1602).

Figure 5:
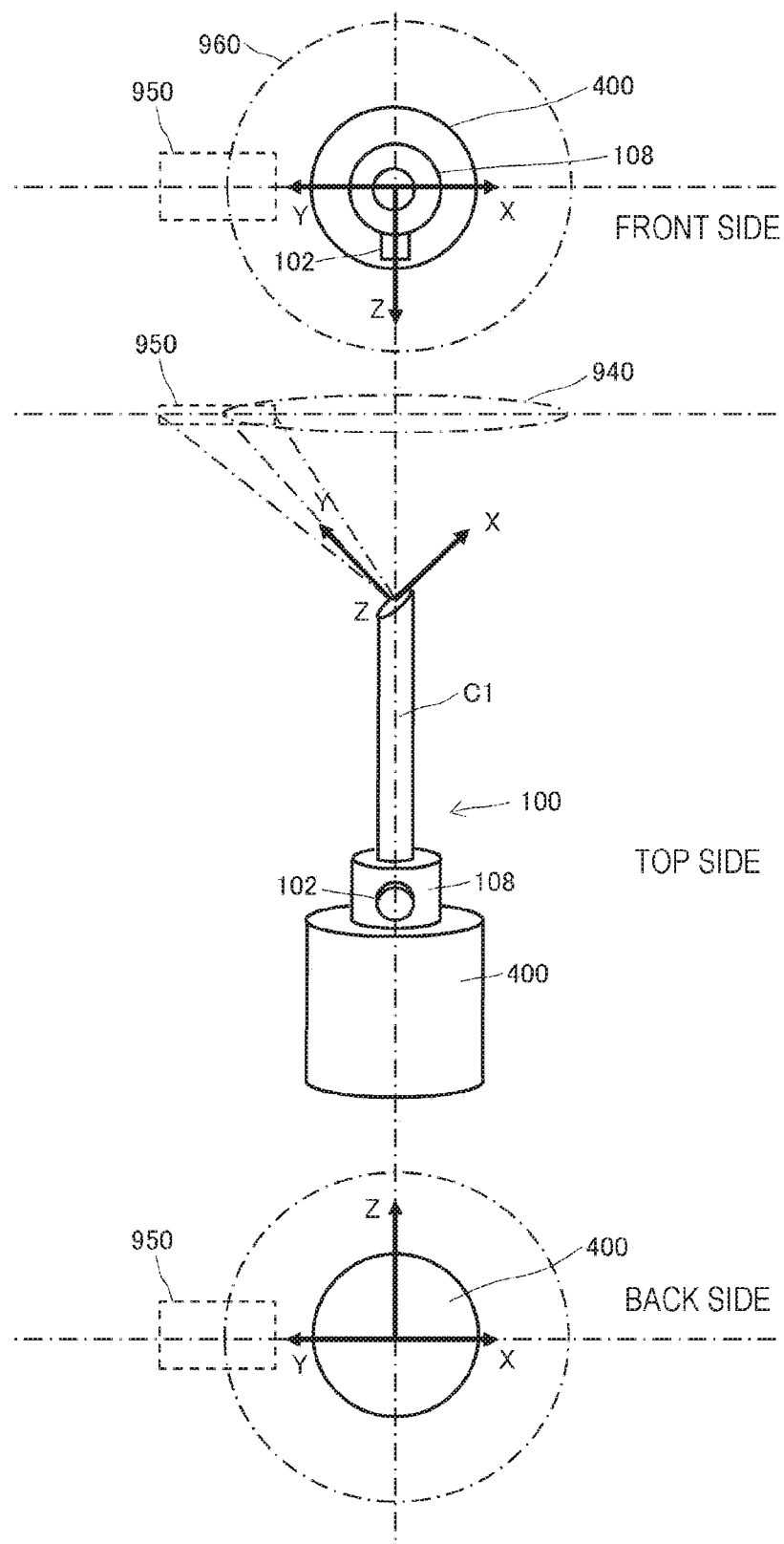
FIG. 5 is a diagram schematically illustrating positional relationships viewed from the top side, the front side (tissue of interest 930 side), and the backside (camera 200 side) of an oblique-viewing endoscope 100, respectively.

Further, FIG. 5 schematically illustrates positional relationships viewed from the top side of the oblique-viewing endoscope 100, the front side (on the tissue of interest 930 side) thereof, and the backside of the camera 200, respectively. As illustrated also in FIG. 1, the oblique-viewing endoscope 100 is attached at the tip of the casing 400 storing the camera 200 therein via the eyepiece part 108. The oblique-viewing endoscope 100 and the camera 200 can rotate independently from each other. The oblique-viewing endoscope 100 is rotatably supported around the optical axis C1 of the eyepiece optical system by the holding part 600, and rotates around the optical axis C1 of the eyepiece optical system relative to the holding part 600 by a driving force of the oblique-viewing endoscope rotation apparatus 300. On the other hand, the camera 200 rotates around the optical axis C2 of the shooting optical system relative to the casing 400 by a driving force of the camera rotation apparatus 500.

A plane which is perpendicular to the optical axis C1 of the eyepiece optical system and in which the tissue of interest 930 is present is defined as an operative field plane 940 in FIG. 5. Then, the camera visual field 950 corresponding to the shooting region of the shooting device 204 of the camera 200 is present on the operative field plane 940.

As described above, the optical axis C3 of the objective optical system of the objective lens part 106 is tilted at a predetermined angle relative to the optical axis C1 of the eyepiece optical system. Further, the oblique-viewing endoscope 100 rotates around the optical axis C1 of the eyepiece optical system relative to the holding part 600 and the optical axis C3 of the objective optical system of the objective lens part 106 also rotates around the optical axis C1 of the eyepiece optical system by a driving force of the oblique-viewing endoscope rotation apparatus 300. Due to the rotation of the oblique-viewing endoscope 100, the center of the camera visual field 950 moves while drawing a rotation movement trajectory 960 on the operative field plane 940.

Figure 6:
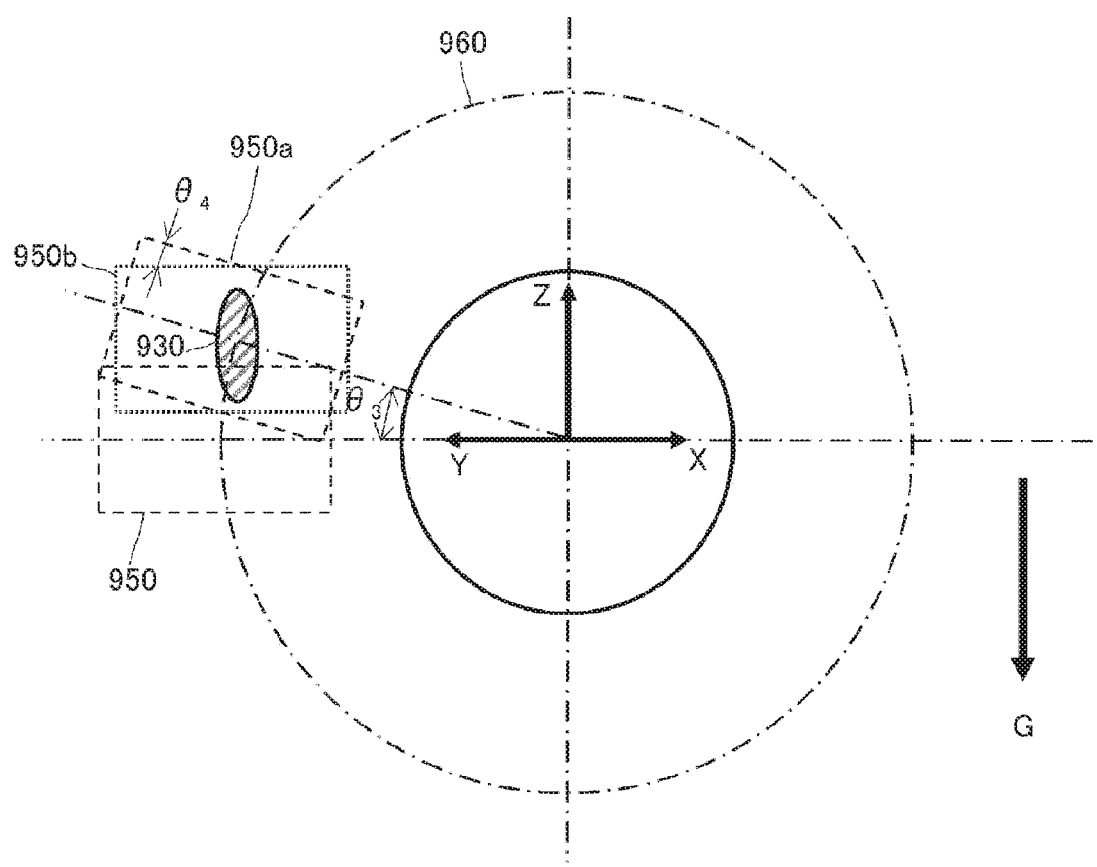
FIG. 6 is a diagram illustrating an enlarged camera visual field 950 indicated on the backside of the oblique-viewing endoscope 100 of FIG. 5.

FIG. 6 illustrates the enlarged camera visual field 950 viewed from the backside of the camera 200 in FIG. 5. In FIG. 6, the position of the camera visual field 950 illustrated in FIG. 5 is assumed as an initial position, and at this time, the tissue of interest 930 is assumed to be present at the illustrated position. Further, FIG. 7 to FIG. 9 illustrate an oblique-viewing endoscope image displayed on the monitor screen 800 and the operator 1100 observing the monitor screen 800. However, in each of FIG. 7 to FIG. 9, it is assumed that the right-hand forceps 900, the left-hand forceps 910, and the oblique-viewing endoscope 100 of the medical observation system 1000 are inserted into the abdominal cavity via the trocars illustrated), respectively. Then, an image acquired by the oblique-viewing endoscope 100 and the camera 200 is displayed on the monitor screen 800 of the display apparatus 168, and the operator 1100 performs a surgery while observing the image on the monitor screen 800.

FIG. 7 illustrates an oblique-viewing endoscope image acquired by the oblique-viewing endoscope 100 and the camera 200 (or an image shot by the shooting device 204) at the initial position of the camera visual field 950. The tissue of interest 930 is captured near the upper edge of the visual field of the camera 200 and only the lower half thereof is displayed on the monitor screen 800 at the initial position illustrated in FIG. 7. The vertical direction of the image on the monitor screen 800 matches with the direction of gravity in this state, and thus it can be said that hand-eye coordination is preferable. However, the optical axis C3 of the objective optical system of the oblique-viewing endoscope 100 faces in a different direction from the tissue of interest 930, and thus only the lower half of the tissue of interest 930 is displayed on the monitor screen as illustrated. The operator 1100 cannot observe the entire tissue of interest 930, and thus the operation is difficult.

Thus, the oblique-viewing endoscope 100 is rotated around the optical axis C1 of the eyepiece optical system by the oblique-viewing endoscope rotation apparatus 300 thereby to put the entire tissue of interest 930 into the visual field of the camera 200. The oblique-viewing endoscope 100 may be rotated around the optical axis C1 of the eyepiece optical system either electrically or manually (as described above).

When the oblique-viewing endoscope 100 is rotated around the optical axis C1 of the eyepiece optical system of the oblique-viewing endoscope 100, the visual field of the camera 200 rotates around the optical axis C1 of the eyepiece optical system and moves to a camera visual field 950a from the initial camera range 950 as illustrated in FIG. 6. Consequently, the tissue of interest 930 is present substantially at the center of the camera visual field 950a after the moving. Thus, the tissue of interest 930 is arranged at the center of the screen and the entire tissue of interest 930 is displayed on the monitor screen 800 as illustrated in FIG. 8.

However, when the oblique-viewing endoscope 100 is rotated, the direction of gravity does not match with the vertical direction of the screen and the oblique-viewing endoscope 100 is tilted. Thus, the tissue of interest 930 is also displayed in a tilted posture not matching with the vertical direction of the screen on the monitor screen 800 as illustrated in FIG. 8.

In the state illustrated in FIG. 8, the operator 1100 is forced to take an action for matching the direction of gravity of the tissue of interest 930 with the vertical direction by, for example, his/her physical operation such as having his/her head bent toward the monitor screen 800. It is difficult for the operator 1100 to perform a surgery on the tissue of interest 930 in an unnatural posture while observing the monitor screen 800 as illustrated in FIG. 8. That is, the operator 1100 cannot keep hand-eye coordination.

Thus, according to the present embodiment, when the oblique-viewing endoscope 100 is rotated around the optical axis C1 of the eyepiece optical system, the casing of the camera 200 is rotated by the camera rotation apparatus 500 such that a relative angle in the direction of gravity and the Z2-axis direction of the shooting optical system is not changed.

When the oblique-viewing endoscope 100 is rotated around the optical axis C1 of the eyepiece optical system of the oblique-viewing endoscope 100 and the shooting device 204 of the camera 200 is rotated around the optical axis C2 of the shooting optical system such that the relative angle in the direction of gravity G and the Z2-axis direction of the shooting optical system is constant, the above camera visual field 950a is rotated to be a camera visual field 950b rotated substantially in parallel with the initial camera range 950 for the visual field of the camera 200 as illustrated in FIG. 6.

The tissue of interest 930 is present substantially at the center of the camera visual field position 950b, and the direction of gravity of the tissue of interest 930 matches with the vertical direction of the screen. Thus, the tissue of interest 930 is arranged at the center of the screen and the entire tissue of interest 930 is displayed in a correct posture matching with the vertical direction of the screen on the monitor screen 800 as illustrated in FIG. 9.

In the state illustrated in FIG. 9, the operator 1100 can operate the right-hand forceps 900 and the left-hand forceps 910 with the left hand, while observing in the state where the direction of gravity of the tissue of interest 930 matches with the vertical direction of the screen. The direction of gravity does not change in its display coordinate system on the monitor screen 800, and the positional relationship between the right-hand forceps 900 and the left-hand forceps 910 on both the right and left hands does not change on the screen of the monitor screen 800. Thus, the operator 1100 can perform a treatment while preferable hand-eye coordination is secured.

The control apparatus 150 will be subsequently described. The control apparatus 150 roughly includes an oblique-viewing endoscope rotation angle acquisition part 152, a gravity direction acquisition part 154, a camera rotation angle calculation part 156, a camera rotation angle control part 158, an oblique-viewing endoscope rotation angle control part 162, the arm control part 164, and an image signal processing part 166. Further, the control apparatus 150 is connected with the UI part 160 and the display apparatus 168. The control apparatus 150 may be integral with the medical observation system 1000 (or the support arm apparatus 700), or may be an information processing apparatus (such as personal computer or server apparatus) connected with the medical observation system 1000 (or the support arm apparatus 700) in a wireless or wired manner.

The gravity direction acquisition part 154 acquires the direction of gravity G. The gravity sensor 170 is attached on the casing 400 of the camera 200. The gravity direction acquisition part 154 acquires the direction of gravity G on the basis of a detected value of the gravity sensor 170. The gravity direction acquisition part 154 may acquire the direction of gravity using other method such as model calculation.

The oblique-viewing endoscope rotation angle acquisition part 152 acquires a rotation angle of the oblique-viewing endoscope 100. The oblique-viewing endoscope rotation angle acquisition part 152 can acquire a rotation angle of the oblique-viewing endoscope 100 with reference to the direction of gravity G acquired by the gravity direction acquisition part 154. Specifically, the oblique-viewing endoscope rotation angle acquisition 152 acquires a rotation angle of the oblique-viewing endoscope 100 (an angle $\theta_3$ indicated in FIG. 6) relative to the horizontal direction (the XY plane of the eyepiece optical system) with respect to the direction of gravity G illustrated in FIG. 6. The oblique-viewing endoscope rotation apparatus 300 includes the angle sensor for detecting a rotation angle of the motor (as described above). Thus, a reference position (horizontal direction) relative to the direction of gravity is previously defined so that the oblique-viewing endoscope rotation angle acquisition 152 can detect the angle $\theta_3$ relative to the horizontal direction from a detected value of the angle sensor.

The camera rotation angle calculation part 156 calculates a rotation angle of the camera rotation apparatus 500 on the basis of the rotation angle of the oblique-viewing endoscope 100 relative to the direction of gravity. The camera rotation angle calculation part 156 can calculate a rotation angle of the camera rotation apparatus 500 with reference to the direction of gravity based on the angle $\theta_3$ acquired by the oblique-viewing endoscope rotation angle acquisition 152. Specifically, the camera rotation angle calculation part 156 calculates a rotation angle (an angle $\theta_4$ indicated in FIG. 6) of the camera 200 relative to the horizontal direction (the XY plane of the shooting optical system) with reference to the direction of gravity G. Angle $\theta_3=\theta_4$ is assumed as illustrated in FIG. 6.

The camera rotation angle control part 158 controls the camera rotation apparatus 500 on the basis of the rotation angle $\theta_4$ of the camera rotation apparatus 500 calculated by the camera rotation angle calculation part 156. As described above, the camera rotation angle control part 158 rotates the casing of the camera 200 by the camera rotation apparatus 500 such that the relative angle in the direction of gravity G and the Z2-axis direction of the shooting optical system does not change when the oblique-viewing endoscope 100 is rotated around the optical axis C1 of the eyepiece optical system.

The UI part 160 is configured of one or more input apparatuses by which the operator 1100 as a user of the medical observation system 1000 inputs an instruction for the medical observation system 1000. The input apparatuses applied for the UI part 160 can be a controller (including a remote controller) including a plurality of operators (such as buttons), a touch panel, a joystick, and the like. A controller such as a remote controller can be mounted on a grip part (such as handle of operation forceps (as described below)) of an operation instrument held by the operator, for example, and a control signal based on an input operation on the operators is transmitted to the control apparatus 150 in a wired or wireless manner. Of course, typical input apparatuses in a computer, such as mouse and keyboard, may be used for the UI part 160.

Further, according to the present embodiment, the UI part 160 includes a microphone capable of collecting user's voice, and various inputs are made also by a recognition result of the voice collected via the microphone. The UI part 160 is able to input information in a non-contact manner so that a user especially in a clean area, such as an operator or an operator's support staff, can operate a device in a non-clean area in a non-contact manner. Further, the user can instruct a device operation without releasing his/her gripping instrument such as forceps, and user convenience enhances and operation efficiency enhances.

Further, a wristwatch-type or glasses-type wearable device capable of being worn on a human body can be used for the UI part 160. The wearable device includes a camera capable of detecting a motion of a user himself/herself or a motion of his/her line of sight or other device, and can detect a user's gesture or a motion of his/her line of sight. Various inputs are made in response to a user's gesture or a motion of his/her line of sight detected by this kind of wearable device. The UI part 160 includes a wearable device, and thus the user in the clean area can operate a device in the non-clean area in a non-contact manner. Further, the user can instruct a device operation without releasing his/her holding instrument such as forceps, and user's convenience enhances. Additionally, a sensing system for detecting a user's gesture or his/her line of sight is additionally provided instead of a wearable device, thereby enabling the user in the clean area to operate a device in the non-clean area in a non-contact manner.

When performing a surgery by use of the medical observation system 1000, the user such as an operator or an operator's support staff can input various items of information associated with the surgery such physical information of a patient or surgery procedure via the UI part 160. Further, the user can input an instruction to drive the arm part 701 of the support arm apparatus 700, an instruction to change a shooting condition of the camera 200 (such as the kind of irradiation light from a light source, magnification, and focal length), and the like via the UI part 160.

Further, the present embodiment assumes that the part 160 can receive an instruction to change an image range displayed on the monitor screen 800 or a camera visual field of the oblique-viewing endoscope 100 and the camera 200. To change the camera visual field includes to move the camera visual field either vertically or horizontally (operation of moving forward/backward and pivot of the oblique-viewing endoscope 100 on the trocar point), to rotate the oblique-viewing endoscope 100 around the optical axis C1 of the eyepiece optical system (including clockwise rotation and counterclockwise rotation), to change the magnification, and the like. The UI part 160 may include a plurality of operators such as buttons for individually receiving the instructions from the user.

The oblique-viewing endoscope rotation angle control part 162 controls a rotation angle of the oblique-viewing endoscope rotation apparatus 300 in response to an operation of the operator 1100 or the like. For example, when the operator 1100 instructs to rotate the oblique-viewing endoscope 100 clockwise or counterclockwise via the UI part 160, the oblique-viewing endoscope rotation angle control part 162 controls the rotation angle of the oblique-viewing endoscope rotation apparatus 300. Additionally, when the oblique-viewing endoscope 100 is rotated around the optical axis C1 of the eyepiece optical system, the camera rotation angle control part 158 rotates the casing of the camera 200 by the camera rotation apparatus 500 such that the direction of gravity G of an object always matches with the vertical direction of the screen irrespective of the rotation angle (as described above).

The arm control part 164 controls a motion of the support arm apparatus 700 attached with the medical observation system 1000 at the distal end. Specifically, the arm control part 164 controls driving the actuator provided at each joint part of the arm pail 701 thereby to control the rotation angle of each joint part, to accordingly control driving the arm part 701, and to consequently realize controlling the position and the posture of the medical observation system 1000 (or the oblique-viewing endoscope 100).

For example, when the operator 1100 instructs to move the camera visual field vertically or horizontally via the UI part 160, the arm control part 164 controls a motion of the support arm apparatus 700 such that an image acquired by the oblique-viewing endoscope 100 and the camera 200 moves in the instructed direction. However, the oblique-viewing endoscope 100 is inserted into the abdominal cavity via the trocar or the motions of the arm part 701 are limited due to the trocar point, and thus it is noted that the camera visual field cannot be moved vertically or horizontally by simply moving the position of the distal end.

Further, when the operator 1100 instructs to change the magnification of an image displayed on the monitor screen 800 via the UI part 160, the arm control part 164 controls a motion of the support arm apparatus 700 such that the objective lens part 106 of the oblique-viewing endoscope 100 is at a distance from the tissue of interest 930 depending on the magnification. A forward-viewing endoscope is moved forward or backward in the optical axis C1 direction of the eyepiece optical system thereby to easily adjust the distance from the tissue of interest 930. However, it should be sufficiently understood for the oblique-viewing endoscope 100 that the optical axis C3 of the objective optical system of the objective lens part 106 is tilted relative to the optical axis C1 of the eyepiece optical system, and thus the optical axis C3 of the objective optical system moves in parallel with the C1 direction when the oblique-viewing endoscope 100 is moved forward or backward in the optical axis C1 direction of the eyepiece optical system, but the distance from the tissue of interest 930 cannot be adjusted.

When changing the position and the posture of the oblique-viewing endoscope 100, the arm control part 164 drives and controls the actuator of each joint part of the support arm apparatus 700 such that an object to be observed is kept at the center of an image shot by the camera 200 (or the optical axis of the objective optical system is kept facing an object to be observed).

The arm control part 164 may control the support arm apparatus 700 in any system of position control system or force control system. However, the force control system may be more preferable since the medical observation system 1000 and the support arm apparatus 700 are for medical use, they operate close to an operator, his/her assistant, or the like in a narrow operation room, and interpersonal physical interaction is desired to realize.

In a case where the force control system is employed for the support arm apparatus 700, the arm control part 164 receives an external force from the user, and drives the actuator of each joint part such that the arm part 701 smoothly moves according to the external force. The arm control part 164 may perform power assist control. Thereby, the user can move the arm part 701 with a relatively weak force while directly contacting the holding part 600 or the medical observation system 1000 at the distal end. Thus, the user can move the medical observation system 1000 with a more intuitive and easier operation. Further, the position of the medical observation system 1000 (or an observation place of the camera 200 via the oblique-viewing endoscope 100) can be fixed more accurately, and thus the user as an operator can stably; acquire an image of an operative site and smoothly perform a surgery.

Further, in a case where the force control system is employed, the arm control part 164 can calculate a torque instruction value of each joint part for the whole body cooperative control of the support arm apparatus 700 in consideration of exercise purposes and constraint conditions for surgery by computations using generalized inverse kinematics, for example, thereby performing the control. For example, the tongue instruction value of each part of the support arm apparatus 700 can be calculated by computations using generalized inverse kinematics assuming the exercise purposes such as moving the camera visual field of the oblique-viewing endoscope 100 and the camera 200 either vertically or horizontally, and moving forward or backward the objective lens part 106 of the oblique-viewing endoscope 100 toward the tissue of interest 930 depending on the magnification, and the constraint conditions including the fact the oblique-viewing endoscope 100 is inserted into the abdominal cavity via the trocar (not illustrated) (or a position where the oblique-viewing endoscope 100 passes through the trocar point is fixed).

Additionally, see Japanese Patent Application Laid-Open No. 2009-95959 or Japanese Patent Application Laid-Open No. 2010-188471 assigned to the present applicants, for example, about the detailed whole body cooperative control using generalized inverse kinematics.

Further, in a case where the force control system is employed for the support arm apparatus 700, there is a concern about a modelling error such as friction or inertia when performing torque control of each joint part. Thus, the arm control part 164 may realize ideal joint control of the joint part driving actuators by estimating disturbance torque due to the modelling error and correcting the torque instruction value. Additionally, see Japanese Patent Application Laid-Open No. 2009-269102 assigned to the present applicants, for example, about detailed ideal joint control.

On the other hand, in a case where the position control system is employed for the support arm apparatus 700, a position and a posture of the oblique-viewing endoscope 100 at the distal end are determined depending on the exercise purposes such as moving the camera visual field of the oblique-viewing endoscope 100 and the camera 200 either vertically or horizontally and moving forward or backward the objective lens part 106 of the oblique-viewing endoscope 100 toward the tissue of interest 930 depending on the magnification. Then, the position instruction value of each joint part of the support arm apparatus 700 for realizing a desired position of the oblique-viewing endoscope 100 may be calculated on the basis of inverse kinematics computations assuming the constraint conditions including the fact the oblique-viewing endoscope 100 is inserted into the abdominal cavity via the trocar (not illustrated) (or a position where the oblique-viewing endoscope 100 passes through the trocar point is fixed).

The image signal processing part 166 controls processing an image shot by the camera 200 and outputting an image to the display apparatus 168. Specifically, the image signal processing part 166 preforms various image processing including a development processing such as demosaic on an image signal (RAW data) output from the camera 200. Further, the image signal processing part 166 performs a processing of detecting an operation instrument such as forceps displayed on an image shot by the camera 200 for the processing such as operation instrument tracking. The image signal processing part 166 then transmits the image signal subjected to the image processing to the display apparatus 168 to be displayed and output on the monitor screen. Further, the image signal processing part 166 transmits a control signal for controlling the shooting conditions such as magnification or focal length to the camera 200.

The display apparatus 168 displays an image based on the image signal subjected to the image processing by the image signal processing part 166 on the monitor screen under control of the image signal processing part 166. In a case where the medical observation system 1000 is for high-resolution shooting such as 4K or 8K, or for 3D display, the display apparatus 168 for the resolution or display system of the medical observation system 1000 should be used. For example, for high-resolution shooting such as 4K or 8K, the display apparatus 168 with a 55-inch screen size or larger is used thereby to obtain a sense of further immersion. Of course, a plurality of display apparatuses 168 with different resolutions and screen sizes may be equipped depending on the intended use.

First Embodiment

Figure 10:
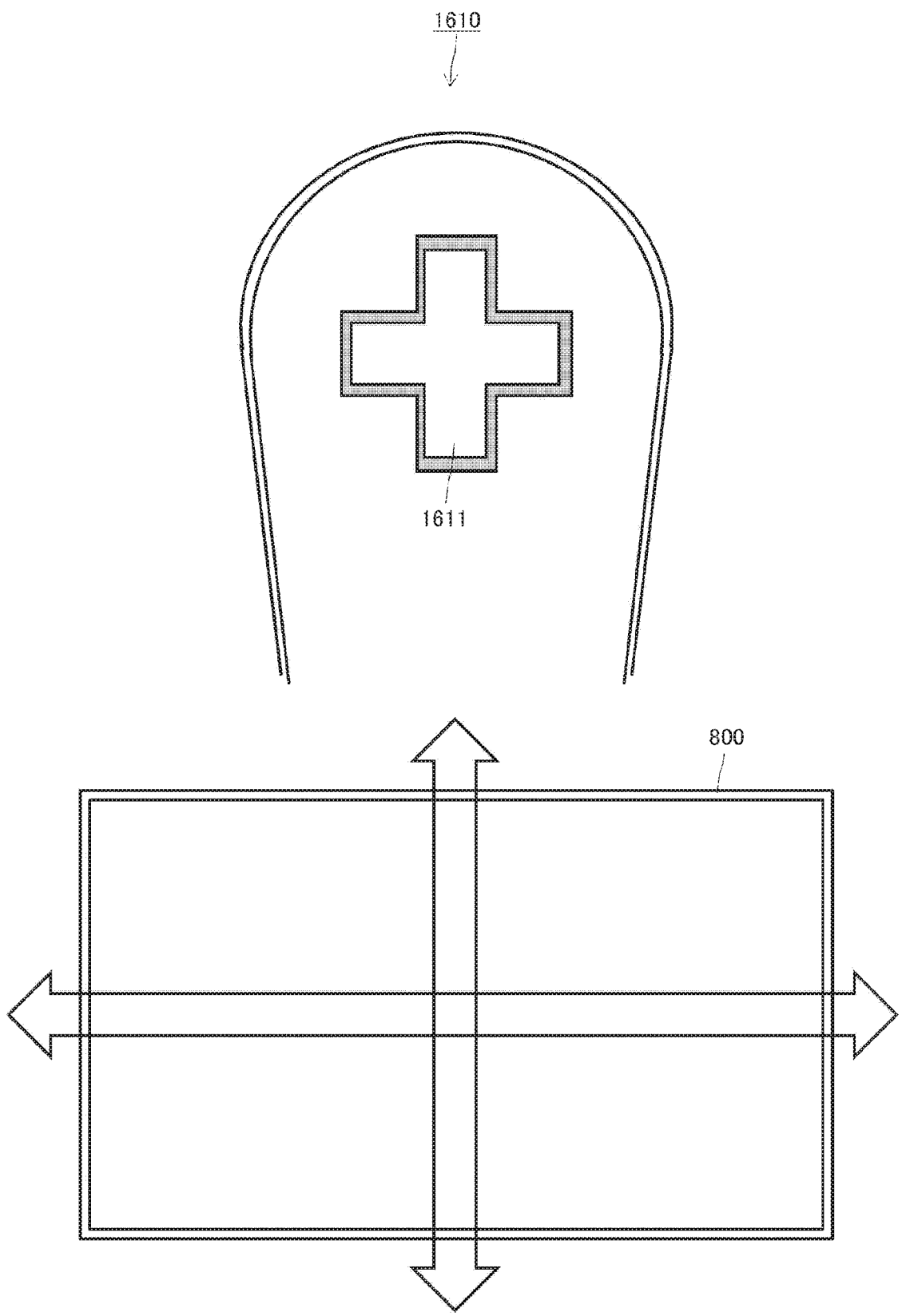
FIG. 10 is a diagram illustrating an exemplary configuration of an input apparatus 1610 applied to a user interface part 160.

FIG. 10 illustrates an exemplary configuration of an input apparatus 1610 applied to the UI part 160. The illustrated input apparatus 1610 includes integrated arrow keys 1611. The illustrated arrow keys 1611 include a vertical key and a horizontal key. A user such as the operator 1100 alternatively presses the upper side or the lower side of the vertical key in the arrow keys 1611 thereby to instruct to move the camera visual field in the upward direction or in the downward direction. Further, he/she alternatively presses the left side or the right side of the horizontal key in the arrow keys 1611 thereby to instruct to move the camera visual field in the leftward direction or the downward direction. However, not the input apparatus 1610 including mechanical buttons such as the arrow keys 1611 but arrow keys displayed on the graphical user interface (GUI) screen may be employed. The user can touch the vertical key or the horizontal key in the GUI-displayed arrow keys or can click them by the mouse.

In a case where the force control system is applied to the support arm apparatus 700 thereby to move the camera visual field in the upward direction or in the downward direction, the arm control part 164 calculates a torque instruction value of each joint part of the support arm apparatus 700 by computations using generalized inverse kinematics assuming as the exercise purposes, moving the camera visual field of the oblique-viewing endoscope 100 and the camera 200 either vertically or horizontally, and the constraint conditions including the fact the oblique-viewing endoscope 100 at the distal end is inserted into the abdominal cavity via the trocar (not illustrated) (or a position where the oblique-viewing endoscope 100 passes through the trocar point is fixed). Then, when each joint part of the support arm apparatus 700 is driven according to the calculated torque instruction value, the display on the monitor screen 800 moves in a direction operated by the arrow keys 1611.

Alternatively, in a case where the position control system is applied to the support arm apparatus 700 thereby to move the camera visual field in the upward direction or in the downward direction, the arm control part 164 determines a position and a posture of the oblique-viewing endoscope 100 at the distal end depending on the exercise purposes of moving the camera visual field of the oblique-viewing endoscope 100 and the camera 200 either vertically or horizontally. Then, a position instruction value of each joint part of the support arm apparatus 700 for realizing a desired position of the oblique-viewing endoscope 100 may be calculated on the basis of inverse kinematics computations assuming the constraint conditions including the fact the oblique-viewing endoscope 100 is inserted into the abdominal cavity via the trocar (not illustrated) (or a position where the oblique-viewing endoscope 100 passes through the trocar point is fixed). Then, when each joint part of the support arm apparatus 700 is driven according to the calculated position instruction value, the display on the monitor screen 800 moves in a direction operated by the arrow keys 1611.

Further, FIG. 11 illustrates other exemplary configuration of an input apparatus 1620 applied for the UI part 160. The illustrated input apparatus 1620 includes four operation buttons 1621 to 1624 arranged in the rightward, leftward, upward, and downward directions, respectively.

A user such as the operator 1100 presses the operation button 1621 arranged on the right side thereby to instruct to rotate the oblique-viewing endoscope 100 clockwise (CW). Similarly, the operation button 1622 arranged on the left side is pressed thereby to instruct to rotate the oblique-viewing endoscope 100 counterclockwise (CCW).

Additionally, when the oblique-viewing endoscope 100 is rotated around the optical axis C1 of the eyepiece optical system, the camera rotation angle control part 158 rotates the casing of the camera 200 by the camera rotation apparatus 500 such that the direction of gravity G of an object always matches with the vertical direction of the screen irrespective of the rotation angle (as described above).

Further, a user such as the operator 1100 presses the operation button 1622 arranged on the upper side thereby to instruct to zoom in an image displayed on the monitor screen 800. Similarly, the operation button 1624 arranged on the lower side is pressed thereby to instruct to zoom out an image displayed on the monitor screen 800.

As described above, when the operator 1100 instructs to change the magnification of an image displayed on the monitor screen 800 via the input apparatus 1620, the arm control part 164 controls a motion of the support arm apparatus 700 such that the objective lens part 106 of the oblique-viewing endoscope 100 is at a distance from the tissue of interest 930 depending on the magnification.

Figure 12:
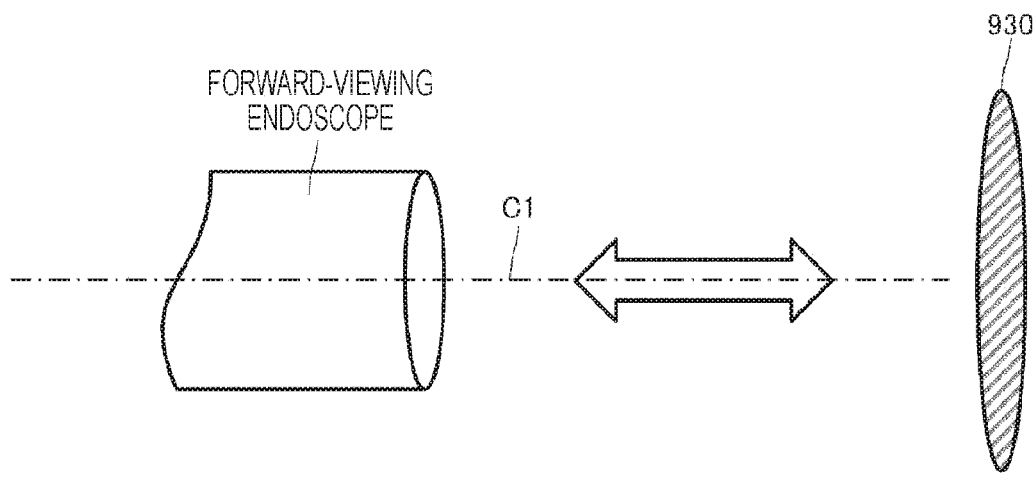
FIG. 12 is a diagram for explaining a method for controlling a motion of the support arm apparatus 700 depending on a change in magnification of an image on the monitor screen 800.

Here, in the case of a forward-viewing endoscope, the optical axis of the objective optical system matches with the optical axis C1 direction of the eyepiece optical system. Thus, as illustrated in FIG. 12, the forward-viewing endoscope is moved forward or backward in the optical axis C1 direction of the eyepiece optical system (or in the longitudinal direction of the forward-viewing endoscope) thereby to easily adjust the distance between the forward-viewing endoscope and the tissue of interest 930 such that the distance therebetween accords to the desired magnification.

Figure 13:
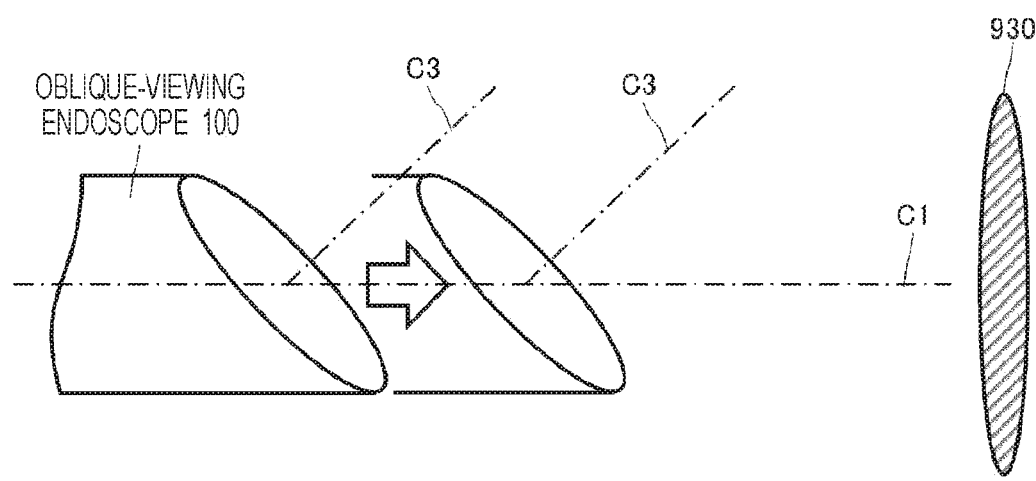
FIG. 13 is a diagram for explaining the method for controlling a motion of the support arm apparatus 700 depending on a change in magnification of an image on the monitor screen 800.

To the contrary, in the case of the oblique-viewing endoscope 100 according to the present embodiment, the optical axis C3 of the objective optical system of the objective lens part 106 is tilted relative to the optical axis C1 of the eyepiece optical system. Thus, when the oblique-viewing endoscope 100 is moved forward or backward in the optical axis C1 direction of the eyepiece optical system (or in the longitudinal direction of the oblique-viewing endoscope 100), the optical axis C3 of the objective optical system moves in parallel with the C1 direction as illustrated in FIG. 13, and the oblique-viewing endoscope 100 does not move forward or backward in the optical axis C3 direction of the objective optical system. That is, even if the oblique-viewing endoscope 100 is simply moved forward or backward in the longitudinal direction, the distance between the oblique-viewing endoscope 100 and the tissue of interest 930 cannot be adjusted to the magnification.

Figure 14:
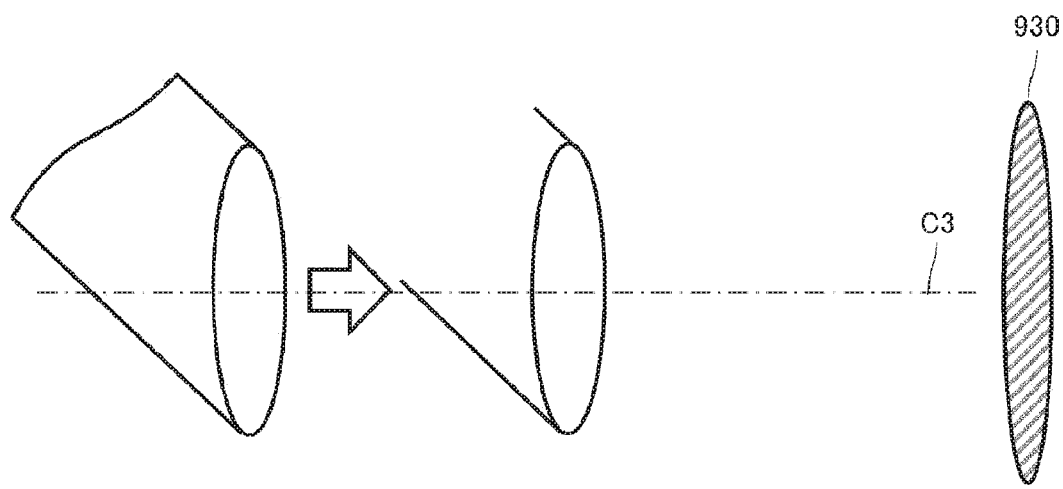
FIG. 14 is a diagram for explaining the method for controlling a motion of the support arm apparatus 700 depending on a change in magnification of an image on the monitor screen 800.
Figure 15:
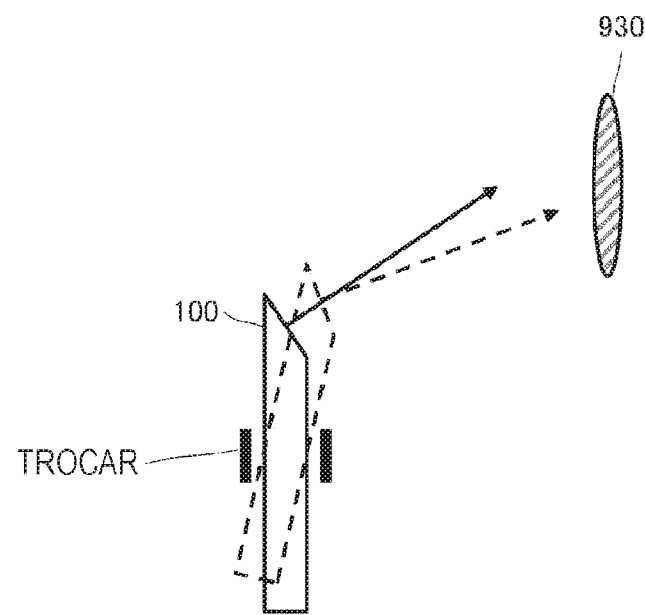
FIG. 15 is a diagram for explaining the method for controlling a motion of the support arm apparatus 700 depending on a change in magnification of an image on the monitor screen 800.

Thus, the distance between the oblique-viewing endoscope 100 and the tissue of interest 930 should be adjusted to accord to a desired magnification not by moving the oblique-viewing endoscope 100 forward or backward in the optical axis C1 direction of the eyepiece optical system but by driving the arm part 701 such that the oblique-viewing endoscope 100 moves forward or backward in the optical axis C3 direction of the objective optical system as illustrated in FIG. 14. Further, assuming the constraint conditions that the oblique-viewing endoscope 100 is inserted into the abdominal cavity via the trocar and pivots on the trocar (or such that a position where the oblique-viewing endoscope 100 passes through the trocar point does not move), the motion of moving in the optical axis C3 direction of the objective optical system as illustrated in FIG. 14 is difficult, and it is realistic to move the oblique-viewing endoscope 100 as similarly to moving in the optical axis C3 direction of the objective optical system as possible in a combination of forward/backward movement of the oblique-viewing endoscope 100 and pivot on the trocar as illustrated in FIG. 15.

In a case where the force control system is applied to the support arm apparatus 700 thereby to change the magnification of an image on the monitor screen 800, the arm control part 164 calculates a torque instruction value of each joint part of the support arm apparatus 700 by computations using generalized inverse kinematics assuming as the exercise purpose, moving the oblique-viewing endoscope 100 forward or backward in the optical axis C3 direction of the objective optical system and the constraint conditions including the fact the oblique-viewing endoscope 100 is inserted into the abdominal cavity via the trocar (not illustrated) (or a position where the oblique-viewing endoscope 100 passes through e trocar point is fixed). Then, when each joint part of the support arm apparatus 700 is driven according to the calculated torque instruction value, the display on the monitor screen 800 is changed to the magnification instructed by the operation key 1623 or 1624.

Alternatively, in a case where the position control system is applied to the support arm apparatus 700 thereby to change the magnification of an image on the monitor screen 800, the arm control part 164 determines a position and a posture of the oblique-viewing endoscope 100 at the distal end depending on the exercise purpose of moving the oblique-viewing endoscope 100 forward or backward in the optical axis C3 direction of the objective optical system. Then, a position instruction value of each joint part of the support arm apparatus 700 for realizing a desired position of the oblique-viewing endoscope 100 may be calculated on the basis of inverse kinematics computations assuming the constraint conditions including the fact the oblique-viewing endoscope 100 is inserted into the abdominal cavity via the trocar (not illustrated) (or a position where the oblique-viewing endoscope 100 passes through the trocar point is fixed). Then, when each joint point of the support arm apparatus 700 is driven according to the calculated position instruction value, the display on the monitor screen 800 is changed to the magnification instructed by the operation key 1623 or 1624.

Additionally, the present applicants think that the user can intuitively and easily understand the above assignments of clockwise, counterclockwise, zoom-in, and zoom-out to the four operation buttons 1621 to 1624, respectively.

Further, not the input apparatus 1610 including mechanical buttons such as the four operation buttons 1621 to 1624 but four operation buttons displayed on the GUI screen may be employed. The user can touch each of the four operation buttons displayed on the GUI screen or can click the same. Further, an operation function assigned to each operation button may be set by the user as needed.

The input apparatus 1610 or 1620 illustrated in FIG. 10 or FIG. 11 can intuitively support the movement of the screen in the vertical and horizontal directions. Further, this is similarly applicable to an input device capable of freely inputting a direction, such as a joystick. By use of a joystick, an instruction to move vertically, horizontally, obliquely, or in any direction or an instruction of a rotation direction can be intuitively made.

On the other hand, in the case of the medical observation system 1000 using the oblique-viewing endoscope 100, a direction in which the oblique-viewing endoscope 100 faces cannot be known only on the screen. If the distal end of the arm part 701 is moved according to an instructed vertical or horizontal moving direction via the input apparatus 1610 or 1620, the screen does not necessarily move in the user's intended direction.

Figure 32:
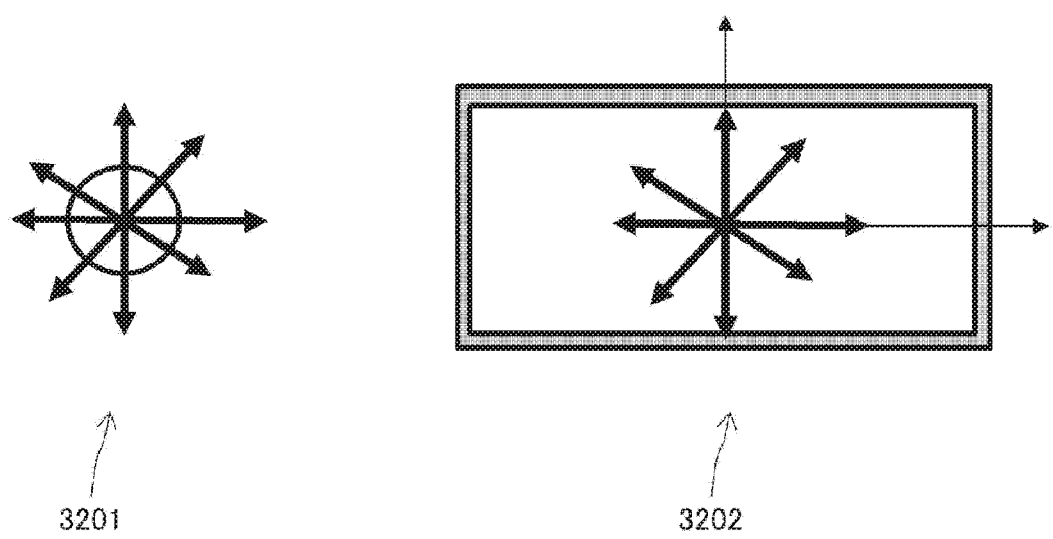
FIG. 32 is a diagram illustrating correspondences between user instructions and screen moving directions.

Thus, the gravity direction acquisition part 154 acquires the correct direction of gravity of the medical observation system 100 from a detection result of the gravity sensor 170, and adjusts the vertical direction of the screen to the direction of gravity on the basis of the posture information of the arm part 701. Then, the rotation angle of each joint part of the arm part 701 and the rotation angle of the camera 200 for realizing the user instructed moving direction of the screen are calculated on the basis of inverse kinematics computations, the arm control part 164 drives and controls the arm part 701, and the camera rotation angle control part 158 drives and controls the rotation angle of the camera 200. In this way, movement 3202 of the screen corresponding to user's direction input 3201 of the screen is realized as illustrated in FIG. 32.

When the screen is instructed to move depending on the rotation direction or the rotation amount of the oblique-viewing endoscope 100, the user cannot know from the screen the direction in which the oblique-viewing endoscope 100 is facing. To the contrary, an instruction in a form of two-degree of freedom of vertical and horizontal is received from the user and the screen is moved according to the user's instruction to move so that the user can intuitively see in a direction which he/she wants to see, and the operability enhances.

Figure 33:
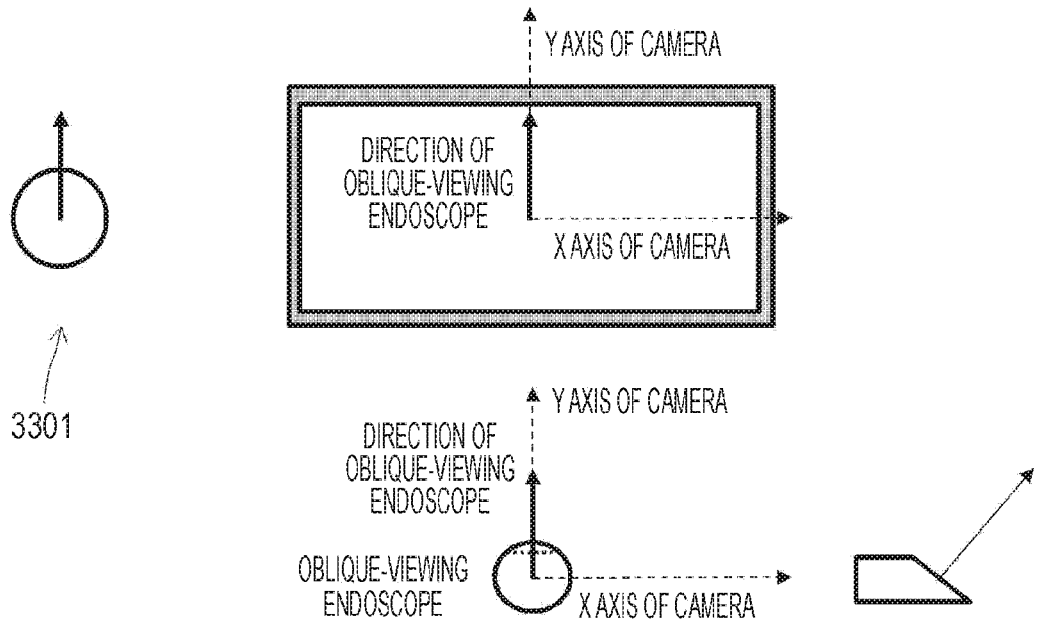
FIG. 33 is a diagram illustrating a correspondence between a user instruction and a direction of the oblique-viewing endoscope.

The XY axes of the camera 200 and the XY axes of the screen are matched. Then, when direction input 3301 of upward direction is made by the user as illustrated in FIG. 33, the camera rotation angle control part 158 rotates and drives the camera 200 such that the line of sight direction of the oblique-viewing endoscope 100 faces in the upward direction on the Y axis of the camera 200. Consequently, the screen moves in the upward direction on the Y axis in which the oblique-viewing endoscope 100 faces.

Figure 34:
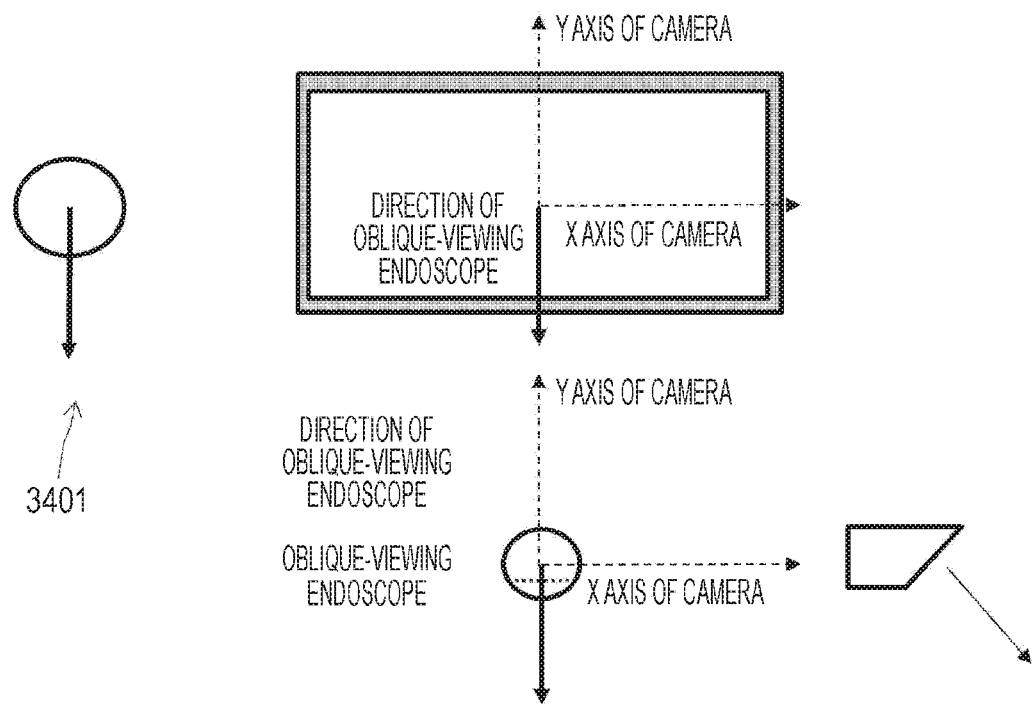
FIG. 34 is a diagram illustrating a correspondence between a user instruction and a direction of the oblique-viewing endoscope.

Further, when direction input 3401 of downward direction is made by the user as illustrated in FIG. 34, the camera rotation angle control part 158 rotates and drives the camera 200 such that the line of sight direction of the oblique-viewing endoscope 100 faces in the downward direction on the Y axis of the camera 200. Consequently, the screen moves in the downward direction on the Y axis in which the oblique-viewing endoscope 100 faces.

Figure 35:
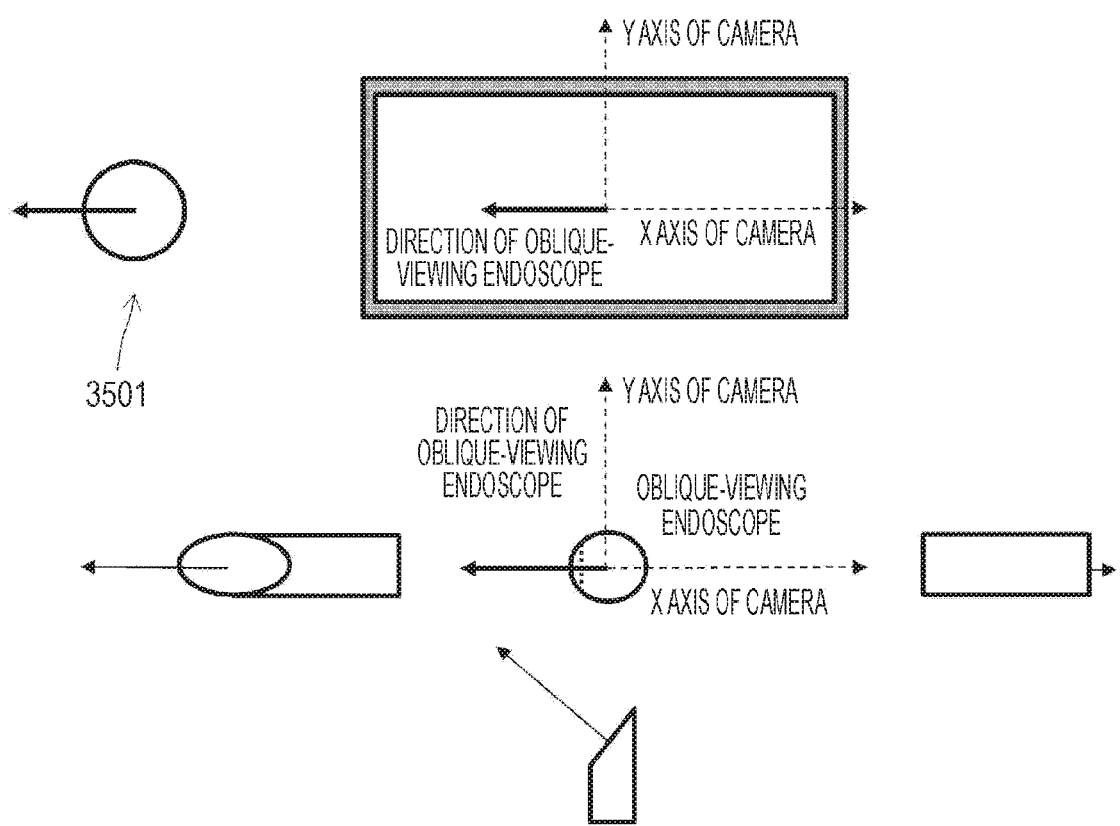
FIG. 35 is a diagram illustrating a correspondence between a user instruction and a direction of the oblique-viewing endoscope.

Further, when direction input 3501 of leftward direction is made by the user as illustrated in FIG. 35, the camera rotation angle control part 158 rotates and drives the camera 200 such that the line of sight direction of the oblique-viewing endoscope 100 faces in the leftward direction on the X axis of the camera 200. Consequently, the screen moves in the leftward direction on the X axis in which the oblique-viewing endoscope 100 faces.

Figure 36:
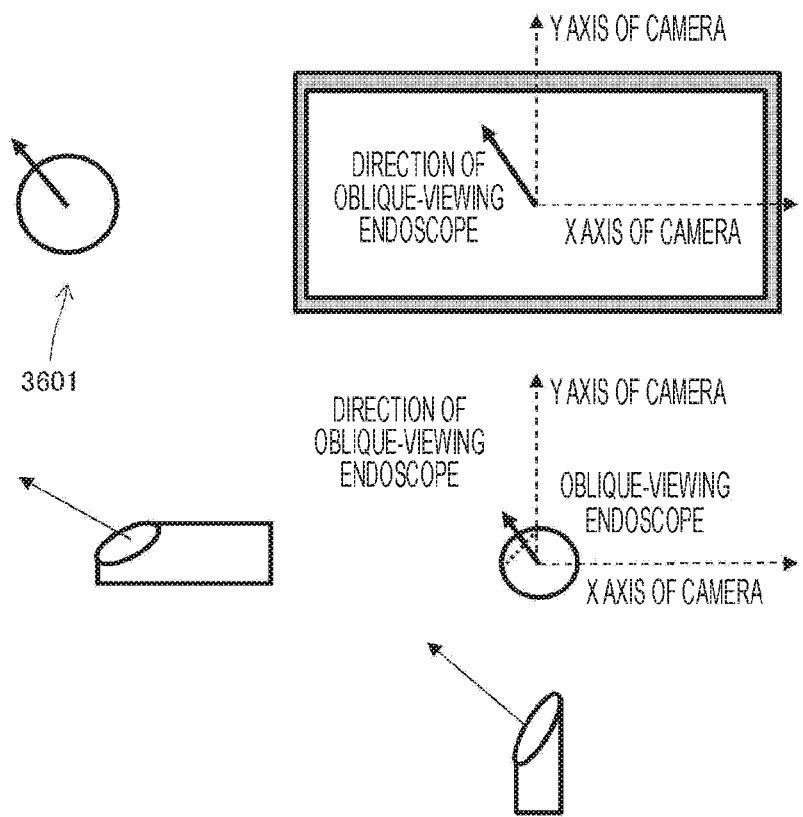
FIG. 36 is a diagram illustrating a correspondence between a user instruction and a direction of the oblique-viewing endoscope.

Further, when direction input 3601 of upper left direction is made by the user as illustrated in FIG. 36, the camera rotation angle control part 158 rotates and drives the camera 200 such that the line of sight direction of the oblique-viewing endoscope 100 faces in the upper left direction. Consequently, the screen moves in the upper left direction in which the oblique-viewing endoscope 100 faces.

Figure 37:
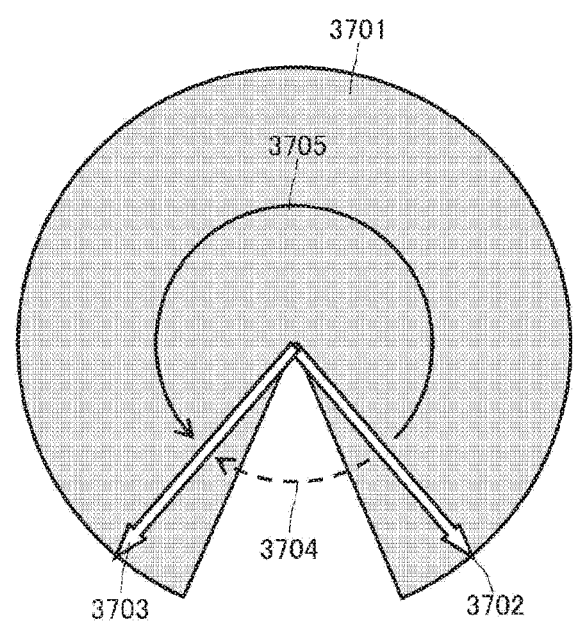
FIG. 37 is a diagram illustrating a behavior when an instruction to rotate beyond a movable range is input for the oblique-viewing endoscope not for permanent rotation.

Here, in a case where the oblique-viewing endoscope 100 is not for 360-degree rotation, when an instruction to rotate beyond a movable range is input by the user, the behavior is problematic. FIG. 37 illustrates an exemplary behavior of the oblique-viewing endoscope 100 when an instruction to rotate beyond a movable range is input by the user. It is assumed that an instruction to rotate and move from a current rotation position 3702 to a rotation position 3703 via a route 3704 is input for the oblique-viewing endoscope 100 with a movable range indicated by a reference numeral 3701. The route 3704 passes outside the movable range 3701, and thus the oblique-viewing endoscope 100 cannot be rotated as the input instruction.

Thus, when the oblique-viewing endoscope 100 not for permanent rotation is instructed to rotate and move beyond the movable range, the oblique-viewing endoscope 100 may be rotated and moved from the current rotation position 3702 to the rotation position 3703 by use of an alternative route passing only inside the movable range 3701 as indicated by a reference numeral 3705 in FIG. 37.

Figure 38:
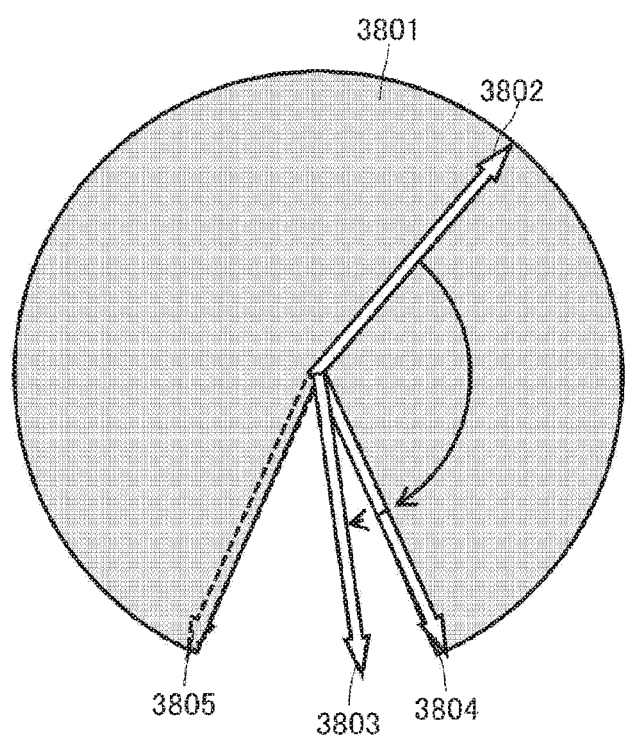
FIG. 38 is a diagram illustrating a behavior when an instruction to rotate outside the movable range is input for the oblique-viewing endoscope not for permanent rotation.

Further, in a case where the oblique-viewing endoscope 100 is not for 360-degree rotation (permanent rotation), also when an instruction to rotate, which causes moving outside the movable range, is input by the user, the behavior is problematic. FIG. 38 illustrates an exemplary behavior of the oblique-viewing endoscope 100 when an instruction to rotate outside a movable range is input by the user. It is assumed that an instruction to rotate and move from a current rotation position 3802 to a rotation position 3803 outside a movable range 3801 is input for the oblique-viewing endoscope 100 with the movable range indicated by a reference numeral 3801. In such a case, the oblique-viewing endoscope 100 can rotate only within the ends of the movable range 3801. Thus, the oblique-viewing endoscope 100 is rotated and moved to an end 3804 closer to the supported rotation position 3803 out of both ends of the movable range 3801. The screen closer to user's request can be presented than in a case where the oblique-viewing endoscope 100 is rotated and moved to the other end 3805 of the movable range 3801.

Second Embodiment

The user can instruct to operate the support arm apparatus 700 holding the medical observation system 1000 via the UI part 160. As described above, the UI part 160 can apply various input devices, and further can use a voice input function, a line of sight input function, and a gesture input function. The present embodiment assumes that an input device (normal UI) such as a remote controller that the user directly operates and an input device (such as natural user interface (NUI)) capable of being operated by user's own operation such as his/her line of sight are used at the same time to perform a complex operation.

Further, in either case where the user uses norma or NUI, the support arm apparatus 700 is not directly instructed to drive the actuator of each joint part of the arm part 701, but is basically instructed by instructing the shooting conditions such as moving the camera visual field of the oblique-viewing endoscope 100 and the camera 200 either vertically or horizontally, magnification, and rotation of the camera 200. Thus, the arm control part 164 calculates an instruction value of each actuator for realizing user-instructed movement of the oblique-viewing endoscope 100 or the camera 200 via UI or NUI on the basis of inverse kinematics computations or the like under the constraint condition that the trocar point through which the oblique-viewing endoscope 100 is inserted is fixed.

Exemplary UI operation commands made by the user by use of normal UI such as a remote controller are listed in the following TABLE 1. It is assumed that the UI part 160 is equipped with operation buttons capable of inputting the commands. The operation buttons may be mechanical operators or buttons on the GUI screen.

TABLE 1

| UI OPERATION COMMAND | OPERATION |
| --- | --- |
| MOVE OPERATION | MOVE IN DESIRED DIRECTION |
| ZOOM OPERATION | ENLARGE |
|  | REDUCE |
| ROTATION OF OBLIQUE-VIEWING ENDOSCOPE (OBLIQUE) | ROTATE AT DESIRED ANGLE AND IN DESIRED DIRECTION |
| UI OPERATION TRIGGER | UI OPERATION START/END TRIGGER |

Figure 18:
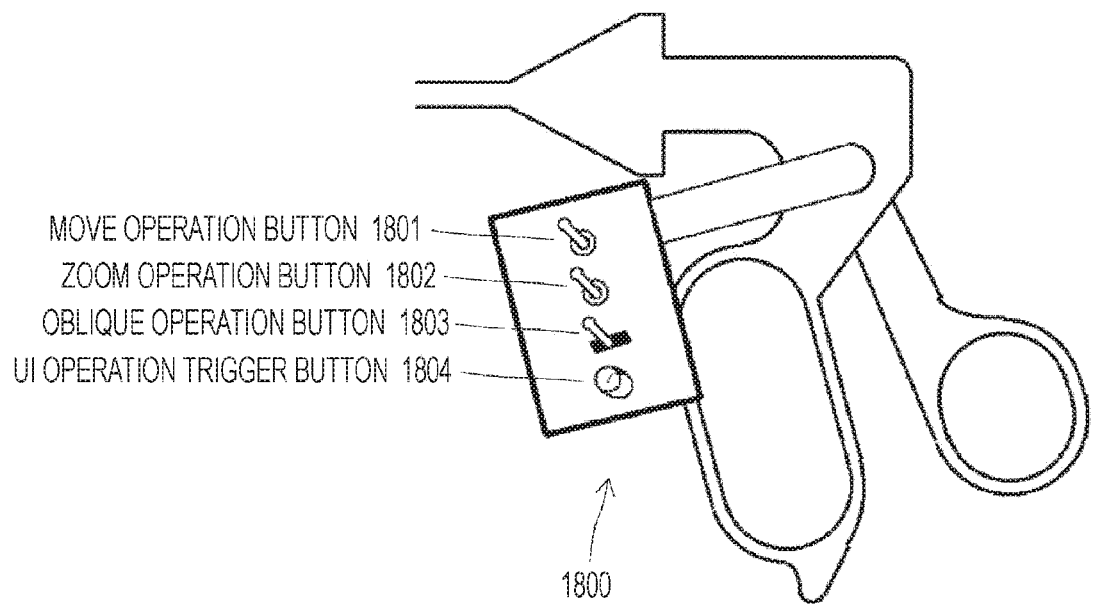
FIG. 18 is a diagram illustrating an appearance configuration of a remote controller mounted on a handle at the root of forceps.

FIG. 18 illustrate an exemplary appearance configuration of a remote controller 1800 which is mounted on a handle at the root of forceps operated by a user as an operator and which can input the operations as indicated in TABLE 1, The illustrated remote controller 1800 includes a MOVE operation button 1801 for instructing to move the camera 200 in the line of sight direction, a ZOOM operation button 1802 for instructing to zoom in/out the camera 200, an OBLIQUE operation button 1803 for instructing to rotate around the optical axis C1 (or C2) of the oblique-viewing endoscope 100, and a UI operation trigger button 1804 for instructing to start the UI operation using the remote controller 1800. The OBLIQUE operation button 1803 is preferably an operator capable of freely inputting a direction in two-degree of freedom.

The UI operation trigger button 1804 is an operation button for instructing to use the remote controller 1800 at the same time with the NUI operation enabling an intuitive operation such as voice or line of sight tracking. Specifically, the UI operation by use of each of the buttons 1801 to 1803 is enabled only while the UI operation trigger button 1804 is being pressed, and the UI operation using each of the buttons 1808 to 1803 is disabled when the UI operation trigger button 1804 is released. The NUI operation such as voice or line of sight tracking and the operation by the remote controller 1800 are used at the same time only while the UI operation trigger button 1804 is being pressed, thereby preventing the arm part 701 from performing an unintended erroneous operation due to unintentional motion of a user's finger during the NUI operation, and realizing a safe complex operation and a safe surgery, Additionally, the UI operation trigger button 1804 may not be on the remote controller 1800 or the like held with a user' hand, but may be a foot switch (not illustrated).

Further, exemplary voice commands capable of being voice-input by the user are listed in the following TABLE 2, Additionally, only the voice commands are listed herein for convenient description, but other NUI commands such as gesture or users line of sight can be used.

TABLE 2

| COMMAND | OPERATION | VOICE |
|---|---|---|
| STOP OPERATING | STOP MOVING | STOP |
|  | STOP MOVING | OK |
| MOVE OPERATION | MOVE UPWARD | Upper |
|  | MOVE DOWNWARD | Lower |
|  | MOVE RIGHTWARD | Right |
|  | MOVE LEFTWARD | Left |
|  | MOVE OBLIQUELY UPWARD TO RIGHT SIDE | Upper Right |
|  | MOVE OBLIQUELY UPWARD TO LEFT SIDE | Upper Reft |
|  | MOVE OBLIQUELY DOWNWARD TO RIGHT SIDE | Lower Right |
|  | MOVE OBLIQUELY DOWNWARD TO LEFT SIDE | Lower Left |
| TRACKING OPERATION (TRACKING FORCEPS/EYES) | TRACK AND MOVE TO TARGET POINT | Track |
| ZOOM OPERATION | ENLARGE | Zoom In, close, push forward |
|  | REDUCE | Zoom Out, farther, pull back |
| OVERVIEW/GOBACK OPERATION (OVERVIEW) | RETURN TO ORIGINAL POSITION AFTER Overview | Overview |
|  | RETURN TO ORIGINAL POSITION AFTER Overview | Turn Back |
| ROTATION OF OBLIQUE-VIEWING ENDOSCOPE (OBLIQUE) | ROTATE IN 1 O'CLOCK DIRECTION | turn 1 |
|  | ROTATE IN 2 O'CLOCK DIRECTION | turn 2 |
|  | ROTATE IN 3 O'CLOCK DIRECTION | turn 3 |
|  | ROTATE IN 4 O'CLOCK DIRECTION | turn 4 |
|  | ROTATE IN 5 O'CLOCK DIRECTION | turn 5 |
|  | ROTATE IN 6 O'CLOCK DIRECTION | turn 6 |
|  | ROTATE IN 7 O'CLOCK DIRECTION | turn 7 |
|  | ROTATE IN 8 O'CLOCK DIRECTION | turn 8 |
|  | ROTATE IN 9 O'CLOCK DIRECTION | turn 9 |
|  | ROTATE IN 10 O'CLOCK DIRECTION | turn 10 |
|  | ROTATE IN 11 O'CLOCK DIRECTION | turn 11 |
|  | ROTATE IN 12 O'CLOCK DIRECTION | turn 12, turn 0 |
|  | OBLIQUE-VIEWING ENDOSCOPE TURNS LEFT | Turn left |
|  | OBLIQUE-VIEWING ENDOSCOPE TURNS RIGHT | Turn Right |
| ACTIVATION WORD | VOICE OPERATION START TRIGGER | hi sony, hey sony |
|  | VOICE OPERATION END TRIGGER | Ok sony, thank you sony |

The respective commands including MOVE, TRACKING, OVERVIEW/GO BACK, ZOOM, and OBLIQUE input via voice or an operation of the remote controller 1800 will be supplementally described. All the commands are for instructing to move or rotate the screen of the display apparatus 168 displaying an image shot by the camera 200 thereon.

MOVE is a command to move the screen of the display apparatus 168 (or an image shot by the camera 200) in a direction designated by voice or the remote controller 1800. The voice commands can designate the eight directions of Upper, Lower, Left, Right, Upper Left, Upper Right, Lower Left, and Lower Right in the MOVE commands as indicated in TABLE 2.

Figures 23, 24:
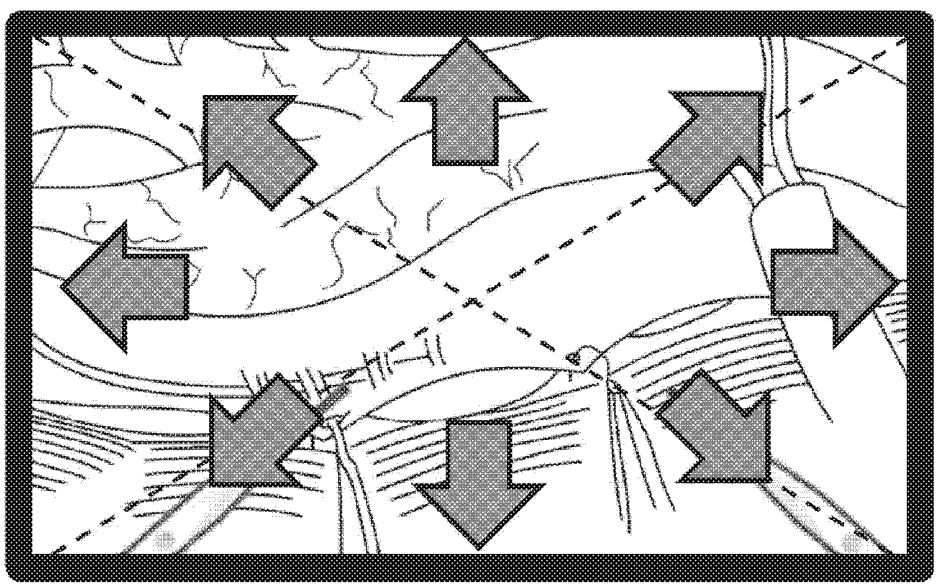
FIG. 23 is a diagram illustrating moving directions designatable by MOVE commands.
FIG. 24 is a diagram illustrating screen moving directions in response to the MOVE commands.
Figure 25:
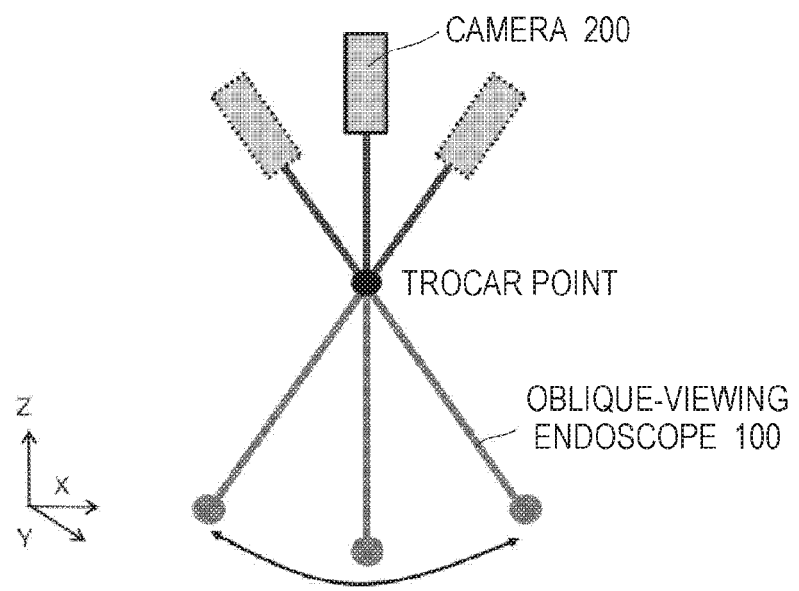
FIG. 25 is a diagram illustrating operations of the oblique-viewing endoscope 100 in response to the MOVE commands.

FIG. 23 illustrates the moving directions designated by the respective MOVE commands of Upper, Lower, Left, Right, Upper Left, Upper Right, Lower Left, and Lower Right. FIG. 24 illustrates the moving directions of the screen in the directions designated by the MOVE commands. Further, FIG. 25 illustrates how the arm part 701 for realizing the MOVE commands operates. As illustrated in FIG. 25, the arm part 701 (not illustrated in FIG. 25) basically operates to rotate the oblique-viewing endoscope 100 with the trocar point as a fulcrum.

Figure 26:
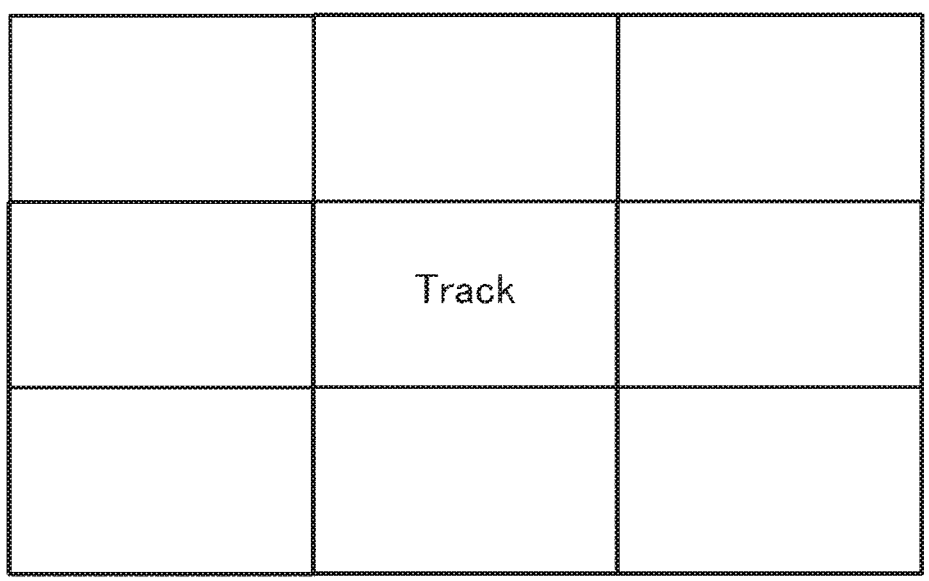
FIG. 26 is a diagram illustrating a screen position displaying a target point in response to a TRACKING command.
Figure 27:
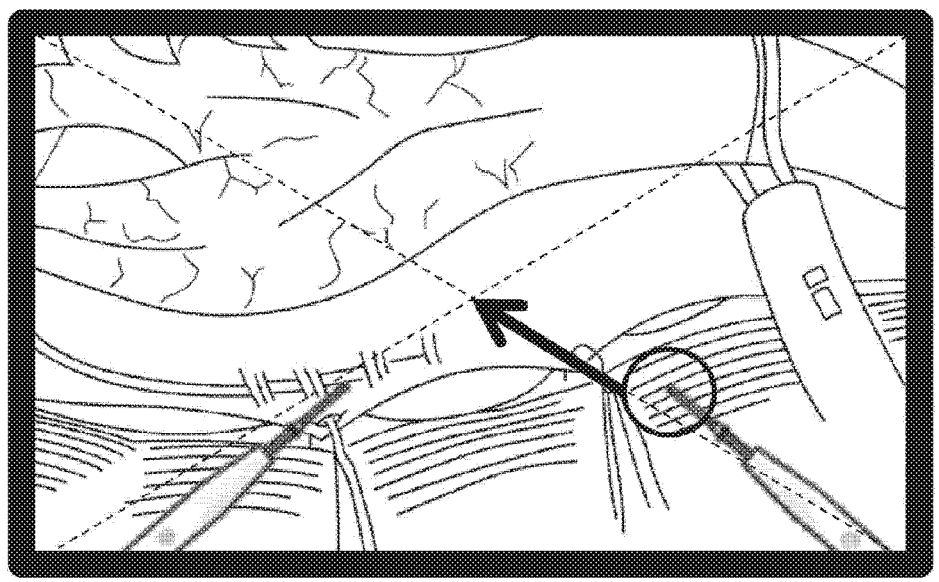
FIG. 27 is a diagram illustrating how the screen racks and moves to the target point.
Figure 28:
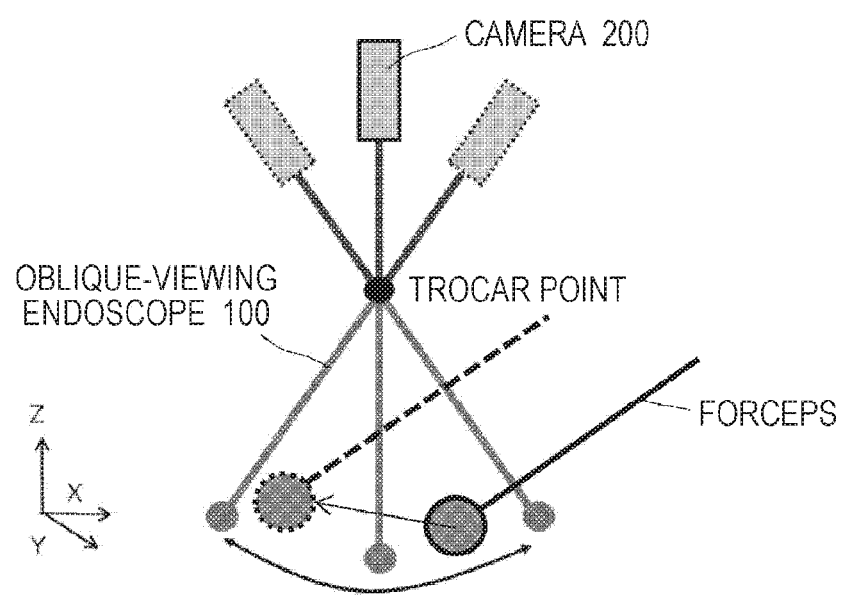
FIG. 28 is a diagram illustrating operations of the oblique-viewing endoscope 100 tracking a target point.

TRACKING is a command to track a target point and move the screen of the display apparatus 168 (or an image shot by the camera 200) thereto. An operation instrument or a line of sight can be set as a target point. FIG. 26 illustrates places on the screen on which a target point is to be displayed. As illustrated in FIG. 26, the screen moves such that an operation instrument or user's line of sight designated as a target point is displayed at the position "Track" at the center of the screen. FIG. 27 illustrates how the screen tracks and moves to a target point. The screen moves in response to the TRACKING command such that an operation instrument designated as the target point is displayed at the center of the screen. Further, FIG. 28 illustrates how the arm part 701 for tracking an operation instrument designated as a target point operates. As illustrated in FIG. 28, the arm part 701 operates to rotate the oblique-viewing endoscope 100 with the trocar point as a fulcrum. Also n a case where not an operation instrument but a user's line of sight is tracked, the arm part 701 similarly operates to rotate the oblique-viewing endoscope 100 with the trocar point as a fulcrum.

OVERVIEW is a command to overview an operative site (or target point). Further, GO BACK is a command to return to the screen before overviewed. The contents of the respective commands OVERVIEW and GO BACK are listed in the following TABLE 3.

TABLE 3

| COMMAND | CONTENTS |
| --- | --- |
| Overview | RETRACT TO TROCAR POINT |
| Go Back | OVERVIEW AND THEN RETURN TO ORIGINAL POSITION |

Figure 29:
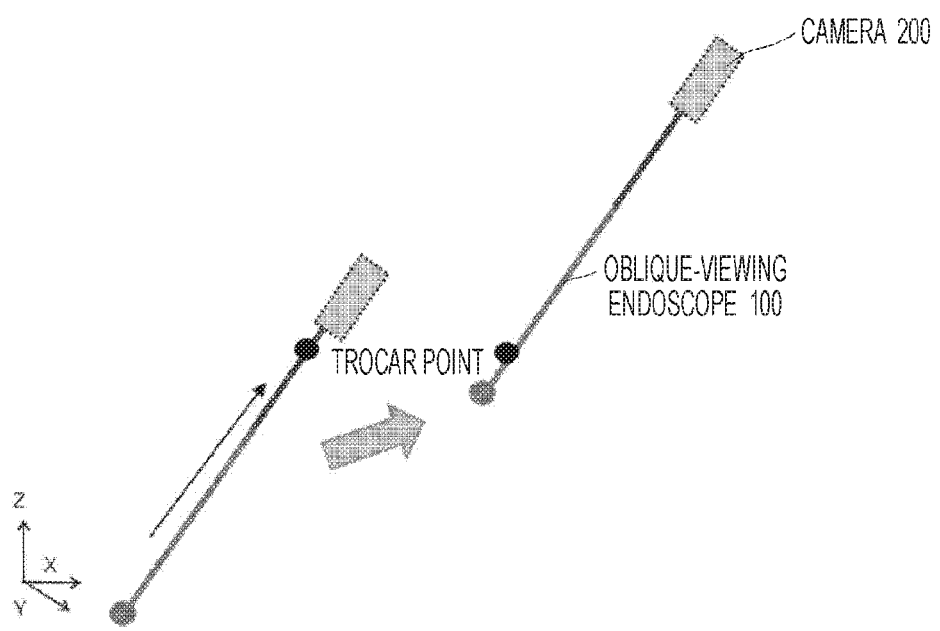
FIG. 29 is a diagram illustrating how the arm part 701 for realizing an OVERVIEW command operates.

FIG. 29 illustrates how the arm part 701 for realizing the OVERVIEW command operates. As illustrated in FIG. 29, the oblique-viewing endoscope 100 is retracted to the trocar point so that the camera 200 can overview and shoot an operative site and the overviewed operative site is displayed on the screen of the display apparatus 168. Further, when the GO BACK command is input after the OVERVIEW command is executed, the oblique-viewing endoscope 100 retracted to the trocar point returns to a position near the original operative site. Thereby, the display apparatus 168 returns to the original screen of the closed (zooming) operative site. Additionally, the operation control of the arm part 701 when executing the OVERVIEW and GO BACK commands is basically similar to that when executing the ZOOM command.

Figure 30:
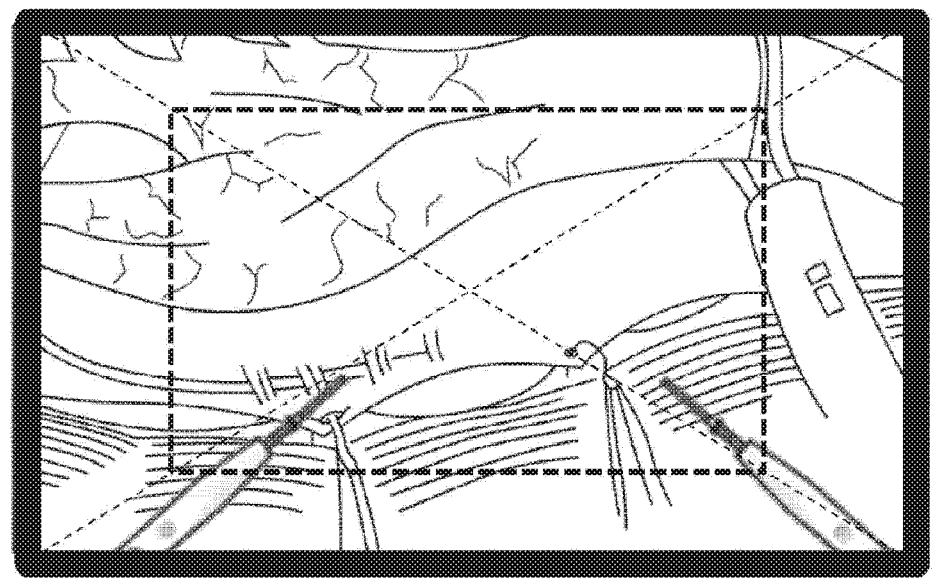
FIG. 30 is a diagram illustrating how the screen is enlarged or reduced in its size in response to a ZOOM command.

ZOOM is a command to enlarge or reduce the screen of the display apparatus 168 (or an image shot by the camera 200). The contents of the commands to enlarge and reduce the screen are listed in the following TABLE 4. "ZOOM IN," "closer," "push forward," and the like are the ZOOM commands to enlarge the screen. Further, "ZOOM OUT," "farther," "pull hack," and the like are the ZOOM commands to reduce the screen. FIG. 30 illustrates how the screen is enlarged or reduced in response to a ZOOM command. When ZOOM IN is instructed, the displayed screen is enlarged such that the rectangular part surrounded by a dotted line in the screen is displayed on the entire screen. Further, when ZOOM OUT is instructed, the entire displayed screen is reduced to the rectangular part surrounded by a dotted line in the screen.

TABLE 4

| VOICE COMMAND | CONTENTS |
| --- | --- |
| ZOOM IN, closer, push forward | CLOSER |
| ZOOM OUT, farther, pull back | FARTHER |

Figure 31:
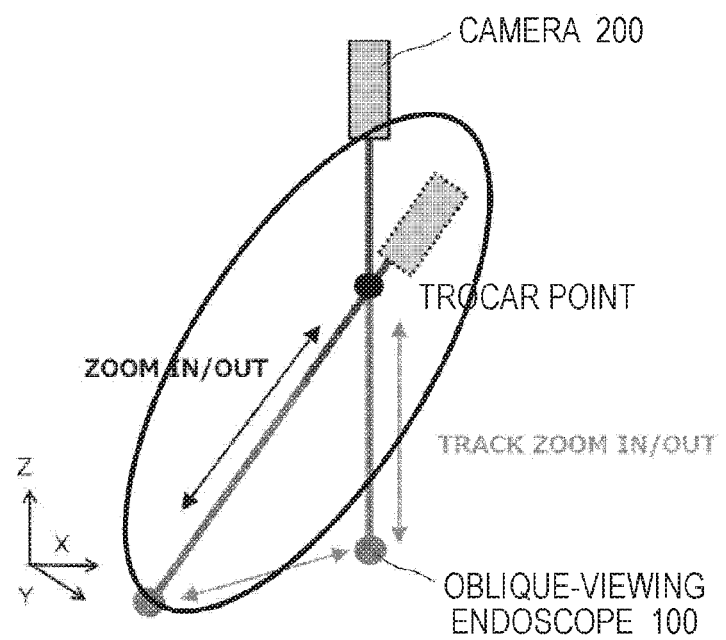
FIG. 31 is a diagram illustrating how the arm part 701 for realizing the ZOOM commands operates.

FIG. 31 illustrates how the arm part 701 for realizing the ZOOM commands operates. Basically, the oblique-viewing endoscope 100 is moved closer to an operative site thereby to enlarge the screen (ZOOM IN) while the oblique-viewing endoscope 100 is moved farther away from an operative site thereby to reduce the screen (ZOOM OUT). As described above with reference to FIG. 13 and FIG. 14, even if the oblique-viewing endoscope 100 is simply moved forward or backward in the longitudinal direction, the distance between the oblique-viewing endoscope 100 and the tissue of interest 930 cannot be adjusted for the magnification. The arm part 701 is driven such that the oblique-viewing endoscope 100 moves forward or backward in the optical axis C3 direction of the objective optical system, thereby realizing ZOOM IN and ZOOM OUT.

Additionally, the operation of moving the oblique-viewing endoscope 100 farther away from an operative site corresponds to the operation of retracing the oblique-viewing endoscope 100 to the trocar point, and thus the operation control of the arm part 701 when executing a ZOOM command may be basically similar to that when executing the OVERVIEW and GO BACK commands.

OBLIQUE is a command to rotate the oblique-viewing endoscope 100. The camera rotation angle control part 158 controls the camera rotation apparatus 500 thereby to realize OBLIQUE. That is, OBLIQUE does not need an operation of the arm part 701, and thus can be executed in parallel with the respective commands MOVE, TRACKING, OVERVIEW/GO BACK, and ZOOM. In a case where an OBLIQUE command is input as a voice command, there are an input method for designating the OBLIQUE command with a parameter indicating a clockwise rotation angle as indicated in TABLE 5 and a method for designating the OBLIQUE command with a parameter indicating a rotation direction (right turn (CW) or left turn (CCW)) as indicated in TABLE 6.

TABLE 5

| VOICE COMMAND | PARAMETER | ROTATION ANGLE |
| --- | --- | --- |
| turn | 1 | IN 1 O'CLOCK DIRECTION |
| | 2 | IN 2 O'CLOCK DIRECTION |
| | 3 | IN 3 O'CLOCK DIRECTION |
| | 4 | IN 4 O'CLOCK DIRECTION |
| | 5 | IN 5 O'CLOCK DIRECTION |
| | 6 | IN 6 O'CLOCK DIRECTION |
| | 7 | IN 7 O'CLOCK DIRECTION |
| | 8 | IN 8 O'CLOCK DIRECTION |
| | 9 | IN 9 O'CLOCK DIRECTION |
| | 10 | IN 10 O'CLOCK DIRECTION |
| | 11 | IN 11 O'CLOCK DIRECTION |
| | 12 | IN 12 O'CLOCK DIRECTION |

TABLE 6

| VOICE COMMAND | PARAMETER | ROTATION DIRECTION |
|---|---|---|
| turn | right | RIGHT TURN (CW) |
| | left | LEFT TURN (CCW) |

Figure 19:
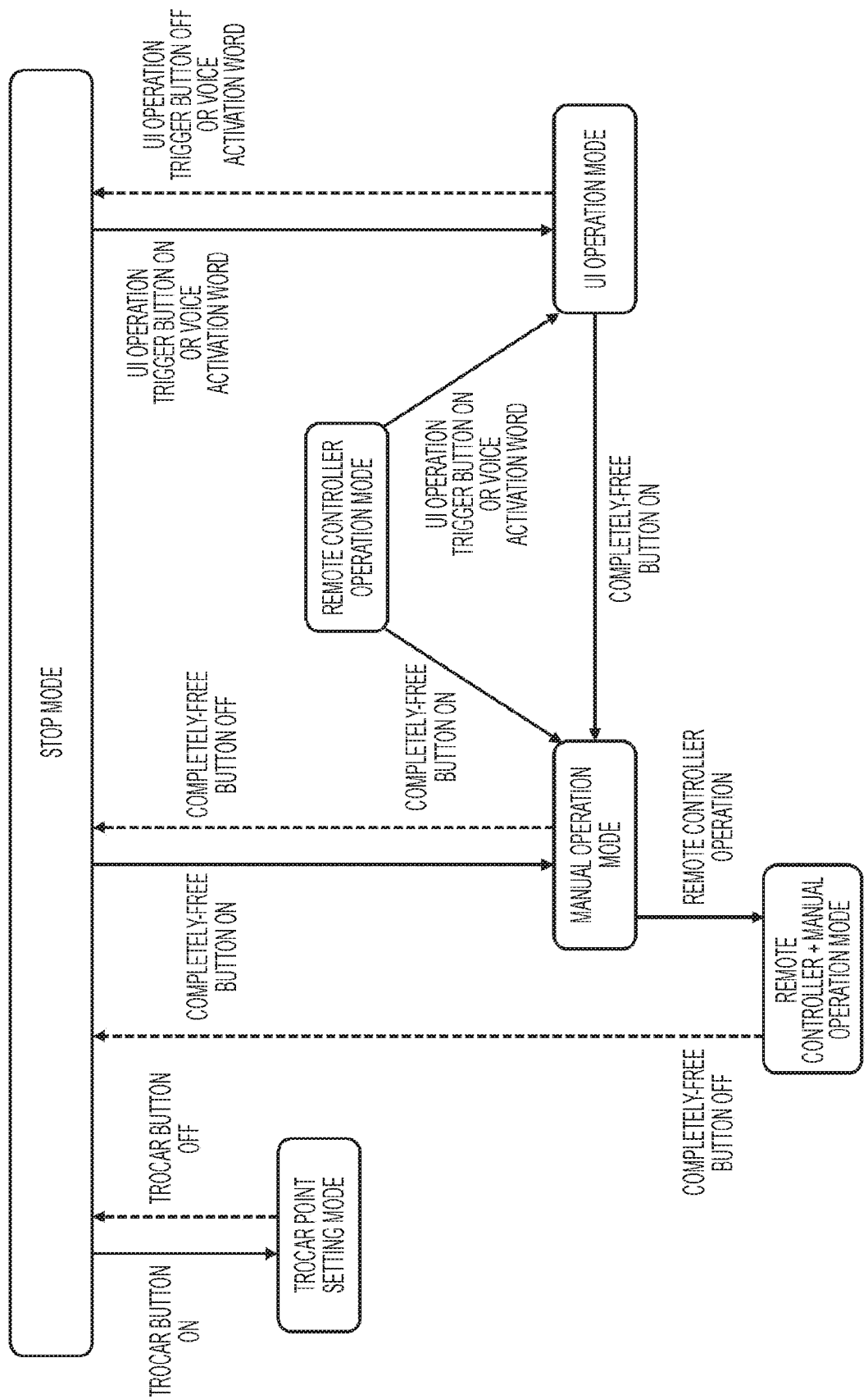
FIG. 19 is a diagram illustrating state transitions of the operation modes of the support arm apparatus 700.

FIG. 19 schematically illustrates state transitions of the operation modes of the support arm apparatus 700. The operation modes of the support arm apparatus 700 include a stop (HOLD) mode, a trocar point setting (TROCAR) mode, a manual operation (MANUAL) mode, a remote controller operation mode (RMTCTRL), and a UI (complex) operation mode.

The stop mode is a state in which the operation of the arm part 701 of the support arm apparatus 700 is completely stopped or fixed.

The trocar point setting mode is an operation mode of setting a fulcrum position (or operation constraint condition) when the oblique-viewing endoscope 100 is inserted into the abdominal cavity of a patient and operated. Basically, the trocar point setting mode is used only at the beginning when the oblique-viewing endoscope 100 is inserted into the abdominal cavity via the trocar. For example, when the trocar button (not illustrated) of the main body of the control apparatus 150 is turned on, the stop mode transits to the trocar point setting mode, and when the trocar button is turned off or the trocar point setting processing is completed, the trocar point setting mode returns to the stop mode. The arm control part 164 stores the position of the trocar measured in the trocar point setting mode.

The manual operation mode is an operation mode in which a user such as an operator directly grips the holding part 600 or the like thereby to manually move the arm part 701 as illustrated in FIG. 2. In the manual operation mode, basically the arm part 701 can freely move the holding part 600 or the tip of the arm to a desired position (completely-free state) while the user hardly feels resistance, and the user can directly grip the holding part 600 or the like thereby to manually move the arm part 701. The arm part 701 keeps the immediately-previous position and posture even if the user releases the holding part 600. For example, when the completely-free button on the main body of the support arm apparatus 700 (or the control apparatus 150) is turned on, the stop mode transits to the manual operation mode, and when the completely-free button is turned off, the manual operation mode returns to the stop mode.

Further, when a key action is performed on the remote controller 1800 in the manual operation mode, the arm part 701 transits to the remote controller+manual operation mode in which the remote controller operation can be performed during completely free. However, only the oblique-viewing endoscope rotation (OBLIQUE) can be operated by the remote controller such that a command inconsistent with the manual operations of the arm part 701 such as MOVE or ZOOM is not received from the remote controller 1800. Then, when the completely-free button is turned off, the remote controller+manual operation mode returns to the stop mode.

The remote controller operation mode is a mode of operating the arm part 701 only by the remote controller 1800. In the remote controller operation mode, operations such as moving the camera 200 in the line of sight direction by use of the MOVE operation button 1801, zooming the camera 200 by use of the ZOOM operation button 1802, and rotating the oblique-viewing endoscope 100 by use of the OBLIQUE operation button 1803 are possible by the remote controller.

For example, when a key action is performed on any of the buttons 1801 to 1803 on the remote controller 1800 in the stop mode, the stop mode transits to the remote controller operation mode, and the remote controller operation mode returns to the stop mode when a predetermined time elapses after the latest operation of the remote controller (or on time-out). Alternatively, a remote controller operation ON button for instructing to start the remote controller operation, a remote controller operation OFF button for instructing to end the remote controller operation, and the like may be arranged on the remote controller 1800, the support arm apparatus 700, or the like.

Further, when the completely-free button on the main body of the support arm apparatus 700 (or the control apparatus 150) is turned on in the remote controller operation mode, the remote controller operation mode transits to the manual operation mode (as described above).

The UI operation mode is an operation mode of performing a complex operation by use of an input device (normal UI) such as a remote controller that the user directly operates, and an input device (such as natural user interface (NUI)) capable of being operated by user's own operation such as voice or line of sight at the same time.

For example, when a voice activation phrase for instructing to start the UI operation such as "Hi Sony" or "Hey Sony" is voice-input or the UI operation trigger button 1804 on the remote controller 1800 is pressed in the stop mode or in the remote controller operation mode, the stop mode or the remote controller operation mode transits to the UI operation mode. Further, when a voice activation phrase for instructing to end the UI operation such as "OK Sony" or "Thank you Sony" is voice-input or the UI operation trigger button 1804 on the remote controller 1800 is released in the UI operation mode, the UI operation mode returns to the stop mode. Further, when the completely-free button on the main body of the support arm apparatus 700 (or the control apparatus 150) is turned on in the UI operation mode, the remote controller operation mode transits to the manual operation mode (as described above).

In the UI operation mode, an operation using the remote controller 1800 is not always possible, the UI operation using each of the buttons 1801 to 1803 is enabled only while the UI operation trigger button 1804 is being pressed, and the UI operation using each of the buttons 1808 to 1803 is disabled when the UI operation trigger button 1804 is released. The simultaneous use of the NUI operation such as voice or line of sight tracking and the operation using the remote controller 1800 is limited only while the UI operation trigger button 1804 is being pressed, thereby preventing the arm part 701 from performing an unintended operation due to an unintentional motion of a user's finger during the NUI operation, and realizing the safe complex operation.

Figure 20:
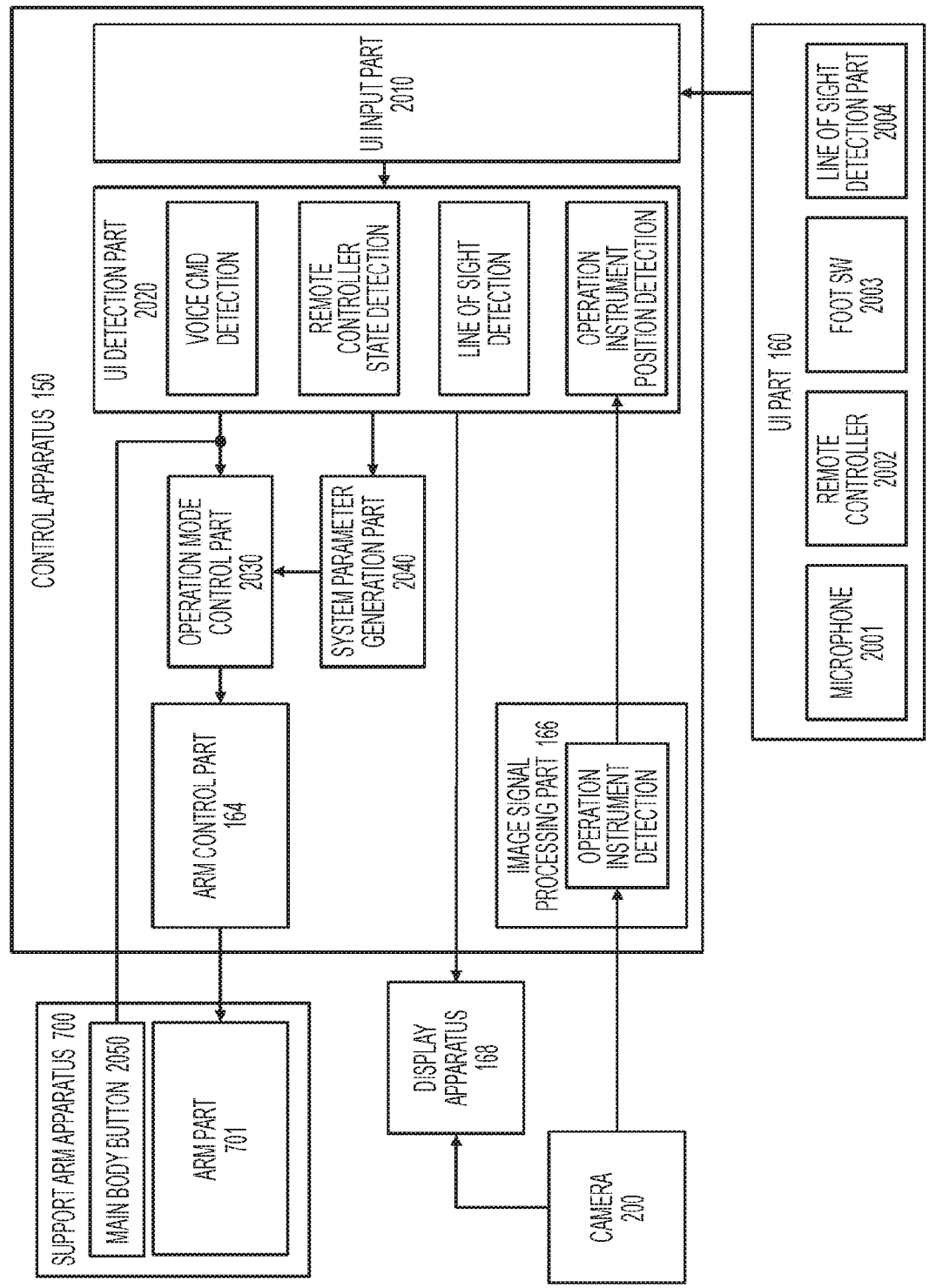
FIG. 20 is a diagram illustrating an exemplary system configuration for realizing control of an arm part 701.

FIG. 20 illustrates a detailed system configuration in which the control apparatus 150 realizes controlling the arm part 701 of the support arm apparatus 700 by way of example. The illustrated system configuration can be for the state transitions of the operation modes illustrated in FIG. 19, and can suitably realize particularly a complex UI operation mode using the normal UI operation and the NUI operation at the same time.

The UI part 160 includes at least a microphone 2001 for collecting user's voice and a remote controller 2002 operated by a user, for example, in order to address the state transitions of the operation modes illustrated in FIG. 19. The remote controller 2002 corresponds to the remote controller 1800 attached on a handle of an operation instrument such as forceps illustrated in FIG. 18, for example. Further, the UI part 160 may include a foot switch 2003 as a UI operation trigger. Further, the UI part 160 preferably includes a line of sight detection part 2004 for detecting a user's line of sight in order to track a line of sight. The line of sight detection part 2004 is configured of a line of sight detection camera equipped on a glasses-type wearable device on a human body, or other sensor for detecting a line of sight mounted or not mounted on a human body, for example.

When receiving a user's input result on the UI part 160 by a UI input part 2010, the control apparatus 150 detects a voice command, a state of the remote controller, a user's line of sight, or the like by the UI detection part 2020. For example, the UI detection part 2020 recognizes user's voice collected by the microphone 2001 thereby to recognize a voice command indicated in TABLE 2, Further, the UI detection part 2020 detects an operation state of each of the buttons 1801 to 1804 on the remote controller 1800 illustrated in FIG. 18.

The oblique-viewing endoscope 100 at the distal end (the holding part 600) of the arm part 701 of the support arm apparatus 700 is inserted into the abdominal cavity of a patient via the trocar (not illustrated), and the camera 200 shoots an operative site via the oblique-viewing endoscope 100.

The image signal processing part 166 controls processing an image shot by the camera 200 and outputting an image to the display apparatus 168. Specifically, the image signal processing part 166 performs various image processing including a development processing such as demosaic on the image signal (RAW data) output from the camera 200. The image signal processing part 166 then transmits the image signal subjected to the image processing to the display apparatus 168 to be displayed and output on the monitor screen.

Further, the image signal processing part 166 performs a processing of detecting an operation instrument such as forceps displayed in an image shot by the camera 200 for a processing such as instrument tracking. The UI detection part 2020 receives an operation instrument detection result from the image signal processing part 166, detects the operation instrument position, and uses the position for the operation instrument tracking operation. However, not the operation instrument detection result but the user's line of sight detection result may be used for the tracking operation. Further, the operation instrument position or the user's line of sight position detected by the UI detection part 2020 may be displayed on the screen of the display apparatus 168 in graphical user interface (GUI) or on screen display (OSD).

A system parameter generation part 2040 determines a dynamic parameter such as the moving amount of the tip of the arm part 701 (or the oblique-viewing endoscope 100) during the tracking operation on the basis of a voice command detection result, a remote controller state detection result, a user's line of sight detection result, or an operation instrument position detection result by the UI detection part 2020.

An operation mode control part 2030 controls the operation modes of the support arm apparatus 700. Specifically, the operation mode control part 2030 controls the operation modes of the support arm apparatus 700 according to the state transitions illustrated in FIG. 19 on the basis of a voice command detection result or a remote controller state detection result by the UI detection part 2020, a user operation on a button 2050 on the main body of the support arm apparatus 700, or the like.

The arm control part 164 controls driving the arm part 701 according to the parameter determined by the system parameter determination part 2040, for example, depending on the operation mode determined by the operation mode control part 2030. For example, when the camera 200 is instructed to move or zoom in a voice command or a remote controller operation, the arm control part 164 calculates an instruction value of each joint part of the arm part 701 on the basis of inverse kinetics computations or the like, and outputs it to the support arm apparatus 700 thereby to change the visual field of the camera 200 as instructed.

The operation mode control part 2030 controls the operation modes of the support arm apparatus 700 according to the state transitions illustrated in FIG. 19. The UI operation mode in the operation modes is an operation mode of performing a complex operation by use of normal UI such as a remote controller that the user directly operates and NUI capable of being operated by user's own operation such as voice or line of sight at the same time.

Figure 21:
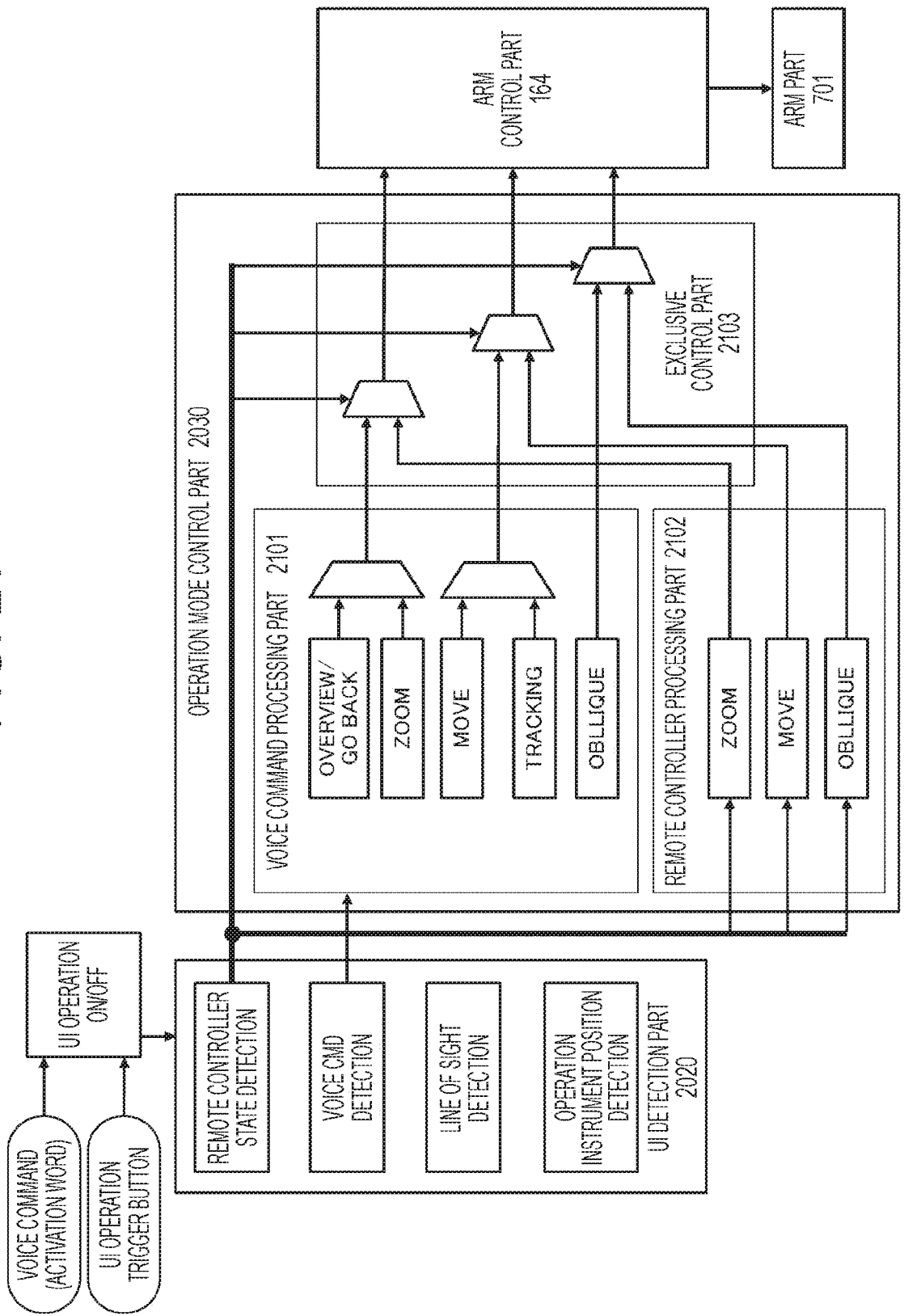
FIG. 21 is a diagram illustrating an exemplary functional configuration of an operation mode control part 2030 for realizing a UI operation mode.

FIG. 21 illustrates an exemplary functional configuration of the operation mode control part 2030 for realizing the UI operation mode. However, the UI operation mode using UI input on the remote controller 1800 and user's voice input at the same time will be referred to herein for simplified description.

The operation mode is switched on/off in response to a voice command from the user or an operation of the UI operation trigger button 1804 on the remote controller 1800. When a voice activation phrase for instructing to start the UI operation such as "Hi Sony" or "Hey Sony" in the stop mode or in the remote controller operation mode is voice-input or the UI operation trigger button 1804 on the remote controller 1800 is pressed, for example, the UI operation mode is switched on. Further, when a voice activation phrase for instructing to end the UI operation such as "OK Sony" or "Thank you Sony" is voice-input or the UI operation trigger button 1804 on the remote controller 1800 is released while the UI operation mode is on, the UI operation mode is switched off.

The operation mode control part 2030 includes a voice command processing part 2101, a remote controller processing part 2102, and an exclusive control part 2103 in order to realize the UT operation mode. When the UT operation mode is switched on, the UI detection part 2020 detects user input on the UI input part 160. Then, when the UI operation mode is switched on, the UI detection part 2020 supplies the user input detection result to the voice command processing part 2101 and the remote controller processing part 2102. Basically, the remote controller 1800's state detection result is supplied to the remote controller processing part 2102 only while the UI operation trigger button 1804 is being pressed.

The voice commands (see TABLE 2) such as "OVERVIEW/GO BACK," "ZOOM," "MOVE," "TRACKING," and "OBLIQUE," which are detected in the voice recognition processing or the like, are input into the voice command processing part 2101. The voice command processing part 2101 then determines a control parameter for driving the arm part 701 in response to an input voice command. "OVERVIEW/GO BACK" and "ZOOM" in the voice commands are similar arm operations, and thus the voice command processing part 2101 integrates the control parameters determined for the respective commands. Further, "MOVE" and "TRACKING" are similar arm operations, and thus the voice command processing part 2101 integrates the control parameters determined for the respective commands.

Further, the remote controller commands (see TABLE 1) such as "ZOOM," "MOVE," and "OBLIQUE" are input into the remote controller processing part 2102 on the basis of a result of the user operation on each of the buttons 1801 to 1803 on the remote controller 1800. The remote controller processing part 210 determines a control parameter for driving the arm part 701 in response to an input remote controller command.

It is assumed that the user inputs the same kind of commands at the same time by voice and an operation of the remote controller 1800. Thus, the exclusive control part 2103 performs command exclusive control to output only the control parameter determined according to one of the voice command or the remote controller command to the arm control part 164.

According to the present embodiment, the exclusive control part 2103 gives priority to and exclusively controls an input command from the remote controller 1800 while the UI operation trigger button 1804 is being pressed. That is, the latter parameter out of a control parameter determined on the basis of the voice command "OVERVIEW/GO BACK" or "ZOOM" in the voice command processing part 2101 and a control parameter determined on the basis of the remote controller operation "ZOOM" in the remote controller processing part 2102 is exclusively output to the arm control part 164 in the same period. Further, the latter parameter out of a control parameter determined on the basis of the voice command "MOVE" or "TRACKING" in the voice command processing part 2101 and a control parameter determined on the basis of the remote controller operation "MOVE" in the remote controller processing part 2102 is exclusively output to the arm control part 164 in the same period. Further, the latter parameter out of a control parameter determined on the basis of the voice command "OBLIQUE" in the voice command processing part 2101 and a control parameter determined on the basis of the remote controller operation "OBLIQUE" in the remote controller processing part 2102 is exclusively output to the arm control part 164 in the same period. However, there is assumed an embodiment in which not the remote controller 1800 but the voice command is given priority for exclusive control.

Figure 22:
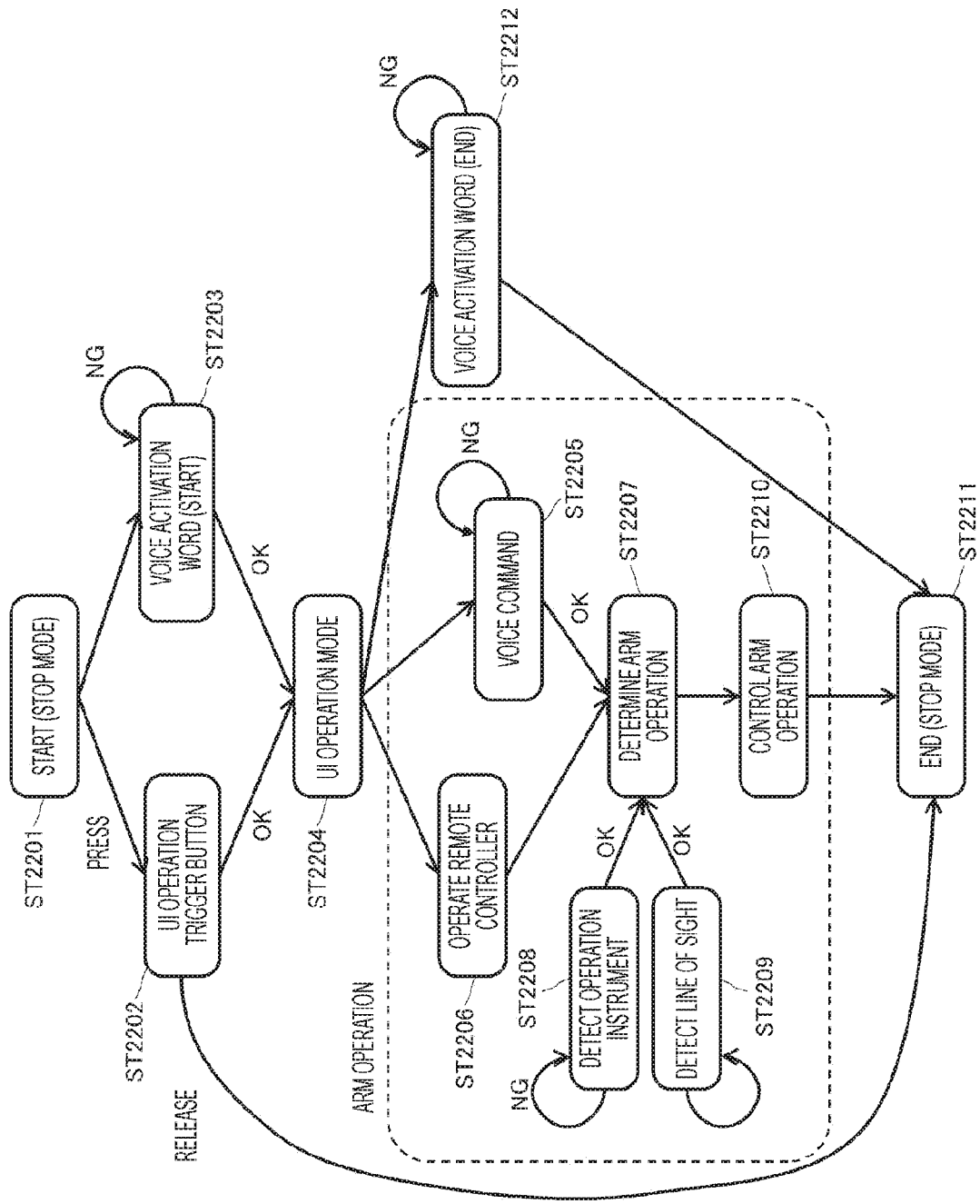
FIG. 22 is a diagram illustrating detailed operation state transitions of the support arm apparatus 700 in the UI operation mode.

FIG. 22 illustrates detailed operation state transitions of the support arm apparatus 700 in the UI operation mode. The operation state transitions can be realized in the functional configuration of the operation mode control part 2030 illustrated in FIG. 21.

The processing proceeds to the UI operation mode (ST2204) when a predetermined voice activation phrase is voice-input by the user (ST2203) or the UI operation trigger button 1804 is pressed on the remote controller 1800 (ST2202) in the stop mode (ST2201). In the UI operation mode, the remote controller operation and the voice command are used at the same time thereby to operate the arm part 701. In the UI operation mode, the user can perform an input operation by use of each of the buttons 1801 to 1803 only while the UI operation trigger button 1804 is being pressed.

In the UI operation mode, when the user inputs a voice command (ST2205), an arm operation for realizing the command is determined (ST2207). Further, in the UI operation mode, when the user presses each of the buttons 1801 to 1803 on the remote controller 1800 (ST2206), an arm operation corresponding to the remote controller operation is determined. Further, when the voice command is input and the remote controller 1800 is operated at the same time, exclusive control is performed such that the operation of the remote controller 1800 is given priority in determining an arm operation (ST2207).

In a case where TRACKING or the tracking operation is instructed by the voice command, the user's line of sight is detected by use of the line of sight detection part 2004 such as line of sight detection camera (ST2208), or the position of an operation instrument in an image shot by the camera 200 is detected (ST2209) thereby to set the user's line of sight or the operation instrument as a target point. Then, an arm operation by which the image shot by the camera 200 tracks and moves to the target point is determined (ST2207).

The arm control part 164 then controls the operation of the arm part 701 on the basis of the determined arm operation (ST2210). Thereafter, when the operation of the arm part 701 is completed, the processing returns to the stop mode (ST2211).

Further, when the UI operation trigger button 1804 is released on the remote controller 1800 (ST2202) or also when the voice activation phrase for instructing to end the UI operation is voice-input in the UI operation mode (ST2212), the processing returns to the stop mode (ST2211).

Additionally, the exemplary medical observation apparatuses in which an endoscope, particularly an oblique-viewing endoscope is mounted on an arm and operated has been described according to the above embodiments, but applications of the present technology are not limited to an oblique-viewing endoscope. That is, the present technology is applicable to medical observation apparatuses in which an optical axis of an eyepiece optical system (a lens tube axis of a scope) does not match with an optical axis of an objective optical system.

For example, the present technology is applicable also to rigid scopes having a tip curving function for enabling a site difficult to see in the body cavity to be observed. In this case, there can arise a situation in which the lens tube axis of the scope does not match with the optical axis of the objective optical system (the optical axis of the tip) due to the curved tip depending on an observation situation during a surgery. Even in such a case, the operability of the apparatus can be enhanced. Additionally, the present technology is of course applicable to a side-viewing endoscope.

Further, the present technology is applicable also to microscopes for surgery, and is advantageous in enhancing the operability in a case where a microscope with an optical axis of an objective optical system tilted relative to a lens tube axis at a predetermined angle is mounted on an arm.

INDUSTRIAL APPLICABILITY

The technology disclosed in the present specification has been described above in detail with reference to specific embodiments. However, it is clear that those skilled in the art can modify or replace the embodiments without departing from the spirit of the technology disclosed in the present specification.

In the present specification, the description has been made mainly with reference to the embodiments in which the technology disclosed in the present specification is applied to a medical system mainly using the robotics technology, but the spirit of the technology disclosed in the present specification is not limited thereto, and is similarly applicable also to force control type robot apparatuses used in medical applications other than surgery or in various fields other than medical field.

Further, in the present specification, the description has been made with reference to the embodiments of a complex operation of the support arm apparatus using the normal UI operation from a remote controller or the like and the NUI operation by voice input, line of sight tracking, or the like at the same time, but the spirit of the technology disclosed in the present specification is not limited to the embodiments. The technology disclosed in the present specification is similarly applicable also to a complex operation in a combination of an operation from an input device other than a remote controller directly operated by the user and NUI by gesture input or the like other than voice input. Further, a complex operation according to the technology disclosed in the present specification can be similarly applied to operations of various medical machines or industrial machines other than the support arm apparatus.

In short, the technology disclosed in the present specification has been described by way of exemplary forms, but the contents described in the present specification should not be interpreted in a limited manner. The scope of CLAIMS should be considered in order to determine the spirit of the technology disclosed in the present specification.

Additionally, the technology disclosed in the present specification can take the following configurations.

(1)
A medical observation system including:
a multi-link structure in which a plurality of inks is mutually coupled by joint parts;
an endoscope attached on the multi-link structure;
a control part configured to control the multi-link structure or the endoscope; and
a user interface part by which a user inputs an instruction to change a visual field of the endoscope,
in which the control part controls the multi-link structure or the endoscope when the user instructs to change the visual field of the endoscope via the user interface part.

(2)
The medical observation system according to (1),
in which the user interface part includes a first operator by which the user inputs an instruction to move the visual field of the endoscope vertically or horizontally, and
the control part controls a motion of the multi-link structure to move the visual field of the endoscope vertically or horizontally according to an operation of the first operator.

(3)
The medical observation system according to (1) or (2),
in which the endoscope is an oblique-viewing endoscope in which an optical axis of an objective optical system is tilted relative to an optical axis of an eyepiece optical system at a predetermined angle and which is rotatable around the optical axis of the eyepiece optical system,
the user interface part further includes a second operator by which the user instructs the visual field direction of the oblique-viewing endoscope, and
the control part controls a rotation angle around a lens barrel axis of the oblique-viewing endoscope according to an operation of the second operator (4)
The medical observation system according to (3),
in which the second operator is an operator configured to input an instruction to move the visual field direction of the endoscope vertically, horizontally, or obliquely.

(5)
The medical observation system according to (3),
in which the control part controls a rotation angle of the oblique-viewing endoscope in a direction corresponding to a coordinate system on a screen on which an image shot by the oblique-viewing endoscope is displayed.

(6)
The medical observation system according to (3),
in which the control part controls a rotation angle of the oblique-viewing endoscope such that the vertical direction of a screen on which an image shot by the oblique-viewing endoscope is displayed is adjusted on the basis of the direction of gravity.

(7)
The medical observation system according to any of (1) to (6),
in which the user n face part further includes a third operator configured to input an instruction to zoom in or out the endoscope, and
the control part is a motion of the multi-link structure to zoom in or out the visual field of the endoscope according to an operation of the third operator.

(8)
The medical observation system according to (7),
in which the endoscope is an oblique: viewing endoscope with an optical axis of an objective optical system tilted relative to an optical axis of an eyepiece optical system at a predetermined angle, and
the control part controls a motion of the multi-link structure such that a distance between the oblique-viewing endoscope and an object to be observed accords to a magnification instructed via the user interface part under a constraint condition that the oblique: viewing endoscope is inserted into the abdominal cavity via a trocar and pivots on the trocar.

(9)
The medical observation system according to any of (1) to (8), further including:
a shooting part configured to shoot an image in the visual field.

(10)
The medical observation system according to any of (1) to (9), further including:
a display apparatus configured to display an image in the visual field.

(11)
A control apparatus including:
a user interface part configured to input an instruction to change a visual field of an endoscope attached on a multi-link structure in which a plurality of links is mutually coupled by joint parts; and
a control part configured to control the multi-link structure or the endoscope,
in which the control part controls the multi-link structure or the endoscope when a user instructs to change the visual field of the endoscope via the user interface part.

(12)
A control method including:
a user input step of inputting an instruction to change a visual field of an endoscope attached on a multi-link structure in which a plurality of links is mutually coupled by joint parts; and
a control step of controlling the multi-link structure or the endoscope,
in which the multi-link structure or the endoscope is controlled in the control step when a user instructs to change the visual field of the endoscope in the user input step.

(21)
A medical observation system including:
an arm capable of holding a medical observation apparatus used for observing a diseased site;
a control part configured to control the arm or the medical observation apparatus; and
a user interface part by which a user inputs an instruction to change a visual field of the medical observation apparatus,
in which the control part controls the arm or the medical observation apparatus in response to an instruction to change the visual field of the medical observation apparatus via the user interface part.

(22)
The medical observation system according to (21),
in which the user interface part includes a first operator by which a user inputs an instruction to move the visual field of the medical observation apparatus in any direction, and
the control part controls a motion of the arm to move the visual field of the medical observation apparatus in a direction corresponding to an instructed moving direction according to an operation of the first operator.

(23)
The medical observation system according to (2)
in which the first operator is an operator configured to input an instruction to move in directions including at least vertically, horizontally, and obliquely.

(24)
The medical observation system according to (21) or (22),
in which the medical observation apparatus is an oblique-viewing endoscope,
the user interface part further includes a second operator by Which a user instructs a visual field direction of the oblique-viewing endoscope, and
the control part controls a rotation angle around a lens tube axis of the oblique-viewing endoscope according to an operation of the second operator.

(25)
The medical observation system according to (24),
in which the second operator is an operator configured to input an instruction to move the visual field direction of the oblique-viewing endoscope in any direction or an instruction rotate the oblique-viewing endoscope clockwise or counterclockwise.

(26)
The medical observation system according to (24),
in which the control part controls a rotation angle of the oblique-viewing endoscope in a direction corresponding to a coordinate system on a screen on which an image shot by the oblique-viewing endoscope is displayed.

(27)
The medical observation system according to (24),
in which the control part controls a rotation angle of the oblique-viewing endoscope such that the vertical direction of a screen on which an image shot by the oblique-viewing endoscope is displayed is adjusted on the basis of the direction of gravity.

(28)
The medical observation system according to any of (21) to (27),
in which the user interface part further includes a third operator configured to input an instruction to zoom in or out the medical observation apparatus, and
the control part controls a motion of the arm to zoom in or out the visual field of the medical observation apparatus according to an operation of the third operator.

(29)
The medical observation system according to (28),
in which the medical observation apparatus is an oblique-viewing endoscope, and
the control part controls a motion of the arm such that a distance between the oblique-viewing endoscope and an object to be observed accords to a magnification instructed via the user interface part under a constraint condition that the oblique-viewing endoscope is inserted into the abdominal cavity via a trocar and pivots on the trocar.

(30)
The medical observation system according to any of (21) to (29), further including:
the medical observation apparatus held by the arm.

(31)
The medical observation system according to any of (21) to (30), further including:
a shooting part configured to shoot an image in the visual field of the medical observation apparatus.

(32)
The medical observation system according to any of (21) to (30), further including:
a display apparatus configured to display an image in the visual field of the medical observation apparatus.

(33)
The medical observation system according to any of (21) to (32),
in which the user interface part includes a controller including at least an operator, and a voice input part, and
the control part controls the arm or the medical observation apparatus according to voice input into the voice input part or an operation of the controller.

(34)
The medical observation system according to (33).
in which the control part starts controlling the arm or the medical observation apparatus by a voice command in response to an input of first activation phrase for instructing to start voice input, and ends controlling the arm or the medical observation apparatus by the voice command in response to an input of second activation phrase for instructing to voice input.

(35)
The medical observation system according to (33) or (34),
in which the control part controls the arm or the medical observation apparatus according to an operation of the controller only while a predetermined trigger button on the controller is being operated.

(36)
The medical observation system according to any of (33) to (35),
in which the control part gives priority to an operation of the controller over the voice command input into the voice input part and controls the arm or the medical observation apparatus.

(37)
The medical observation system according to (36),
in which when the voice input for overviewing or zooming the visual field of the medical observation apparatus and an operation for zooming the visual field of the medical observation apparatus on the controller are performed at the same time, the control part gives priority to an operation on the controller and controls the arm or the endoscope.

(38)

The medical observation system according to (36),
in which when the voice input for moving the visual field of the medical observation apparatus or tracking a predetermined target and an operation for moving the visual field of the medical observation apparatus on the controller are performed at the same time, the control part gives priority to an operation on the controller and controls the arm or the endoscope.

(39)

The medical observation system according to (36),
in which the medical observation apparatus is an oblique-viewing endoscope, and
when the voice input part and the controller are instructed to rotate the oblique-viewing endoscope at the same time, the control part gives priority to an operation on the controller and controls rotating the oblique-viewing endoscope.

(40)

A control apparatus including:
a user interface part configured to input an instruction to change a visual field of a medical observation apparatus held by an arm; and
a control part configured to control the arm or the medical observation apparatus,
in which the control part controls the arm or the endoscope when instructed to change the visual field of the medical observation apparatus via the user interface part.

(41)

A control method including:
a user input step of inputting an instruction to change a visual field of a medical observation apparatus held by an arm; and
a control step of controlling the arm or the medical observation apparatus,
in which the arm or the endoscope is controlled in the control step when an instruction to change the visual field of the medical observation apparatus is made in the user input step.

REFERENCE SIGNS LIST

100 Oblique-viewing endoscope (lens tube)
102 Light guide connector
106 Objective lens part
108 Eyepiece part
150 Control apparatus
152 Oblique-viewing endoscope rotation angle acquisition part
154 Gravity direction acquisition part
156 Camera rotation angle acquisition part
158 Camera rotation angle control part
160 User interface part
162 Oblique-viewing endoscope rotation angle control part
164 Arm control part
166 Image signal processing part
168 Display apparatus
170 Gravity sensor
200 Camera.
204 Shooting device
300 Oblique-viewing endoscope rotation apparatus
400 Casing
500 Camera rotation apparatus
600 Holding part
700 Support arm apparatus
701 Arm part
702 Base part
800 Monitor screen
900 Right-hand forceps
910 Left-hand forceps
930 Tissue of interest
1000 Medical observation system
2001 Microphone
2002 Remote controller
2003 Foot switch
2004 Line of sight detection part
2010 UI input part
2020 UI detection part
2030 Operation mode control part
2040 System parameter generation part
2050 Main body button
2101 Voice command processing part
2102 Remote controller processing part
2103 Exclusive control part

The invention claimed is:

1. A medical observation system comprising:
circuitry configured to
control an arm and an oblique-viewing endoscope arranged at an end of the arm, the arm and the oblique-viewing endoscope being included in the medical observation system used for observing a diseased site;
receive an instruction from a user, via a user interface, to change a visual field of the oblique-viewing endoscope, the visual field of the oblique-viewing endoscope being adjusted to zoom in or out based on the instruction; and
control a motion of the arm such that a distance between the oblique-viewing endoscope and an object to be observed accords to a magnification instructed via the user interface under a constraint condition that the oblique-viewing endoscope is inserted into an abdominal cavity via a trocar and pivots on the trocar, without vending a point of the oblique-viewing endoscope between a contact point of the trocar and an end of the oblique-viewing endoscope in a longitude direction of the oblique-viewing endoscope;
wherein the circuitry is configured to select a trocar point setting mode among a plurality of operation modes to set a fulcrum position for the oblique-viewing endoscope inserted into the abdominal cavity, the plurality of operation modes including at least one of a stop mode, the trocar point setting mode, a manual operation mode, a remote controller operation mode, and a complex operation mode,
wherein the circuitry is configured to select at least one of the manual operation mode, the remote controller operation mode, and the complex operation mode, to control the motion of the arm, after setting the fulcrum position in the trocar point setting mode.

2. The medical observation system according to claim 1, wherein the circuitry is configured to move the visual field of the oblique-viewing endoscope in any direction, and
the circuitry is configured to control the motion of the arm to move the visual field of the oblique-viewing endoscope in a direction corresponding to an instructed moving direction according to an operation received via the user interface.

3. The medical observation system according to claim 2, wherein the circuitry is configured to receive an instruction to move in directions including at least vertically, horizontally, and obliquely.

4. The medical observation system according to claim 1, wherein the circuitry is configured to control a rotation angle around a lens barrel axis of the oblique-viewing endoscope according to an operation received via the user interface.

5. The medical observation system according to claim 4, wherein the instruction is to move the visual field direction of the oblique-viewing endoscope in any direction or to rotate the oblique-viewing endoscope clockwise or counterclockwise.

6. The medical observation system according to claim 4, wherein the circuitry is configured to control a rotation angle of the oblique-viewing endoscope in a direction corresponding to a coordinate system on a screen on which an image shot by the oblique-viewing endoscope is displayed.

7. The medical observation system according to claim 4, wherein the circuitry is configured to control a rotation angle of the oblique-viewing endoscope such that the vertical direction of a screen on which an image shot by the oblique-viewing endoscope is displayed is adjusted on a basis of the direction of gravity.

8. The medical observation system according to claim 1, further comprising:
a camera configured to shoot an image in the visual field of the oblique-viewing endoscope.

9. The medical observation system according to claim 1, further comprising:
a display configured to display an image in the visual field of the oblique-viewing endoscope.

10. The medical observation system according to claim 1, wherein the circuitry is configured to receive the instruction as a voice input via the user interface, and
the circuitry is configured to control the arm or the oblique-viewing endoscope according to the voice input.

11. The medical observation system according to claim 10, wherein the circuitry is configured to start controlling the arm by a voice command in response to an input of first activation phrase for instructing to start voice input, and end controlling the arm by the voice command in response to an input of second activation phrase for instructing to end the voice input.

12. The medical observation system according to claim 11, wherein the circuitry is configured to give priority to an operation of the remote controller over the voice command input via the user interface and control the arm, under a condition that the complex operation mode is selected.

13. The medical observation system according to claim 12, wherein when the voice input for overviewing or zooming the visual field of the oblique-viewing endoscope and an operation for zooming the visual field of the oblique-viewing endoscope on the remote controller are performed at the same time, the circuitry is configured to give priority to the operation on the remote controller and control the arm of the oblique-viewing endoscope, under a condition that the complex operation mode is selected.

14. The medical observation system according to claim 12, wherein when the voice input for moving the visual field of the oblique-viewing endoscope or tracking a predetermined target and an operation for moving the visual field of the oblique-viewing endoscope on the remote controller are performed at the same time, the circuitry is configured to give priority to the operation on the remote controller, and control the arm, under a condition that the complex operation mode is selected.

15. The medical observation system according to claim 12, wherein when an instruction to rotate the oblique-viewing endoscope from the voice input and another instruction to rotate the oblique-viewing endoscope from the remote controller are performed
at the same time, the circuitry is configured to give priority to the other operation from the remote controller and control rotating the oblique-viewing endoscope, under a condition that the complex operation mode is selected.

16. The medical observation system according to claim 10, wherein the circuitry is configured to control the arm according to an operation of a remote controller only while a predetermined trigger button on the remote controller is being operated.

17. The medical observation system according to claim 1, wherein the circuitry is configured to control the arm such that the oblique-viewing endoscope virtually moves forward or backward in an optical axis direction of an objective optical system by a combination of forward/backward movement of the oblique-viewing endoscope and rotation movement of the oblique-viewing endoscope on the fulcrum position on the trocar, to zoom in or out the medical observation apparatus.

18. The medical observation system according to claim 17, wherein the circuitry is configured to calculate a torque instruction value of each joint of a plurality of joints of the arm by computations using generalized inverse kinematics for moving the oblique-viewing endoscope forward or backward in the optical axis direction of the objective optical system, under the constraint condition including the fact the oblique-viewing endoscope is inserted into the abdominal cavity via the trocar.

19. The medical observation system according to claim 17, wherein the circuitry is configured to determine a position and a posture of the oblique-viewing endoscope at a distal end for moving the oblique-viewing endoscope forward or backward in the optical axis direction of the objective optical system, and calculate a position instruction value of each joint of a plurality of joints of the arm for realizing a desired position of the oblique-viewing endoscope on a basis of inverse kinematics computations, under the constraint condition including the fact the oblique-viewing endoscope is inserted into the abdominal cavity via the trocar.

20. A control method comprising:
controlling an arm and an oblique-viewing endoscope arranged at an end of the arm, the arm and the oblique-viewing endoscope being included in the medical observation system used for observing a diseased site;
receiving an instruction from a user, via a user interface, to change a visual field of the oblique-viewing endoscope, the visual field of the oblique-viewing endoscope being adjusted to zoom in or out based on the instruction; and
controlling a motion of the arm such that a distance between the oblique-viewing endoscope and an object to be observed accords to a magnification instructed via the user interface under a constraint condition that the oblique-viewing endoscope is inserted into an abdominal cavity via a trocar and pivots on the trocar, without vending a point of the oblique-viewing endoscope between a contact point of the trocar and an end of the oblique-viewing endoscope in a longitude direction of the oblique-viewing endoscope;

wherein a trocar point setting mode is selected among a plurality of operation modes to set a fulcrum position for the oblique-viewing endoscope inserted into the abdominal cavity, the plurality of operation modes including at least one of a stop mode, the trocar point setting mode, a manual operation mode, a remote controller operation mode, and a complex operation mode, wherein at least one of the manual operation mode, the remote controller operation mode, and the complex operation mode, is selected to control the motion of the arm, after setting the fulcrum position in the trocar point setting mode.

21. A non-transitory computer-readable storage medium including computer executable instructions, wherein the instructions, when executed by a medical observation system, cause the medical observation system to perform a method, the method comprising:

controlling an arm and an oblique-viewing endoscope arranged at an end of the arm, the arm and the oblique-viewing endoscope being included in the medical observation system used for observing a diseased site;

receiving an instruction from a user, via a user interface, to change a visual field of the oblique-viewing endoscope, the visual field of the oblique-viewing endoscope being adjusted to zoom in or out based on the instruction; and controlling a motion of the arm such that a distance between the oblique-viewing endoscope and an object to be observed accords to a magnification instructed via the user interface under a constraint condition that the oblique-viewing endoscope is inserted into an abdominal cavity via a trocar and pivots on the trocar, without vending a point of the oblique-viewing endoscope between a contact point of the trocar and an end of the oblique-viewing endoscope in a longitude direction of the oblique-viewing endoscope;

wherein a trocar point setting mode is selected among a plurality of operation modes to set a fulcrum position for the oblique-viewing endoscope inserted into the abdominal cavity, the plurality of operation modes including at least one of a stop mode, the trocar point setting mode, a manual operation mode, a remote controller operation mode, and a complex operation mode, wherein at least one of the manual operation mode, the remote controller operation mode, and the complex operation mode, is selected to control the motion of the arm, after setting the fulcrum position in the trocar point setting mode.

* * * * *